(12) United States Patent
Takaai et al.

(10) Patent No.: US 8,623,994 B2
(45) Date of Patent: Jan. 7, 2014

(54) METHOD FOR PRODUCING WATER ABSORBENT RESIN

(75) Inventors: Toshihiro Takaai, Himeji (JP); Shinichi Fujino, Himeji (JP); Hidenori Wada, Himeji (JP)

(73) Assignee: Nippon Shokubai, Co., Ltd. (JP)

( * ) Notice: Subject to any disclaimer, the term of this patent is extended or adjusted under 35 U.S.C. 154(b) by 0 days.

(21) Appl. No.: 13/574,271

(22) PCT Filed: Jan. 20, 2011

(86) PCT No.: PCT/JP2011/051003
§ 371 (c)(1),
(2), (4) Date: Jul. 20, 2012

(87) PCT Pub. No.: WO2011/090129
PCT Pub. Date: Jul. 28, 2011

(65) Prior Publication Data
US 2012/0289671 A1 Nov. 15, 2012

(30) Foreign Application Priority Data

Jan. 20, 2010 (JP) ................................ 2010-009812
Mar. 12, 2010 (JP) ................................ 2010-055236
Mar. 31, 2010 (JP) ................................ 2010-084024

(51) Int. Cl.
*C08G 63/02* (2006.01)

(52) U.S. Cl.
USPC .................... 528/481; 206/524.6; 252/194

(58) Field of Classification Search
USPC ........................... 206/524.6; 252/194
See application file for complete search history.

(56) References Cited

U.S. PATENT DOCUMENTS

| | | | |
|---|---|---|---|
| 4,920,202 A | 4/1990 | Irie et al. | |
| 5,005,771 A | 4/1991 | Pieh et al. | |
| 5,229,487 A | 7/1993 | Tsubakimoto et al. | |
| 5,945,495 A | 8/1999 | Daniel et al. | |
| 6,187,902 B1 | 2/2001 | Yanase et al. | |
| 6,207,796 B1 | 3/2001 | Dairoku et al. | |
| 6,291,636 B1 | 9/2001 | Miyake et al. | |
| 6,641,064 B1 | 11/2003 | Dentler et al. | |
| 6,906,159 B2 | 6/2005 | Dairoku et al. | |
| 7,682,702 B2 | 3/2010 | Nitschke | |
| 7,960,490 B2 | 6/2011 | Funk et al. | |
| 2006/0167198 A1 | 7/2006 | Sasabe et al. | |
| 2007/0123624 A1 | 5/2007 | Otten et al. | |
| 2007/0232760 A1 | 10/2007 | Fujimaru et al. | |
| 2008/0021150 A1 | 1/2008 | Becker et al. | |
| 2008/0214749 A1 | 9/2008 | Weismantel et al. | |
| 2008/0287631 A1 | 11/2008 | Nitschke | |
| 2009/0157027 A1 | 6/2009 | Kamphus et al. | |
| 2009/0208748 A1 | 8/2009 | Torii et al. | |
| 2009/0321682 A1* | 12/2009 | Kajikawa et al. | 252/194 |
| 2010/0001233 A1 | 1/2010 | Funk et al. | |
| 2010/0016522 A1 | 1/2010 | Stueven et al. | |
| 2010/0041549 A1 | 2/2010 | Weismantel et al. | |
| 2010/0249320 A1 | 9/2010 | Matsumoto et al. | |

FOREIGN PATENT DOCUMENTS

| | | |
|---|---|---|
| JP | 54-053165 | 4/1979 |
| JP | 57-198714 | 12/1982 |
| JP | 7-270070 | 10/1995 |
| JP | 8-073518 | 3/1996 |
| JP | 10-059534 | 3/1998 |
| JP | 2000-143720 | 5/2000 |
| JP | 2001-018222 | 1/2001 |
| JP | 2002-226599 | 8/2002 |
| JP | 2003-012812 | 1/2003 |
| JP | 2006-160774 | 6/2006 |
| JP | 2006-199862 | 8/2006 |
| JP | 2006199862 * | 8/2006 |
| JP | 2007-224224 | 9/2007 |
| JP | 2007-291351 | 11/2007 |
| JP | 2009-142728 | 7/2009 |
| JP | 2009-545635 | 12/2009 |
| WO | 2007/057350 | 5/2007 |
| WO | 2007/116778 | 10/2007 |
| WO | 2008/034786 | 3/2008 |
| WO | 2008/037676 | 4/2008 |
| WO | 2008/087114 | 7/2008 |
| WO | 2009/028568 | 3/2009 |

OTHER PUBLICATIONS

Fredric L. Buchholz and Andrew T. Graham, The Modern Superabsorbent Polymer Technology (1998), pp. 87-93.

* cited by examiner

*Primary Examiner* — Terressa Boykin
(74) *Attorney, Agent, or Firm* — Cesari and McKenna, LLP

(57) ABSTRACT

With regard to a method for producing a water absorbent resin by drying a particulate hydrogel crosslinked polymer having a high solid content concentration (of 45% by weight or more, further 50% by weight or more, and particularly 55% by weight or more), to provide a method for efficient drying of a water absorbent resin having maintained/improved physical properties.
A production method in which a through-circulation belt type dryer or a through-circulation stationary batch type dryer is used in the drying step and the drop and scatter ratio of a particulate hydrogel crosslinked polymer is set to 1% by weight or less.

18 Claims, 1 Drawing Sheet

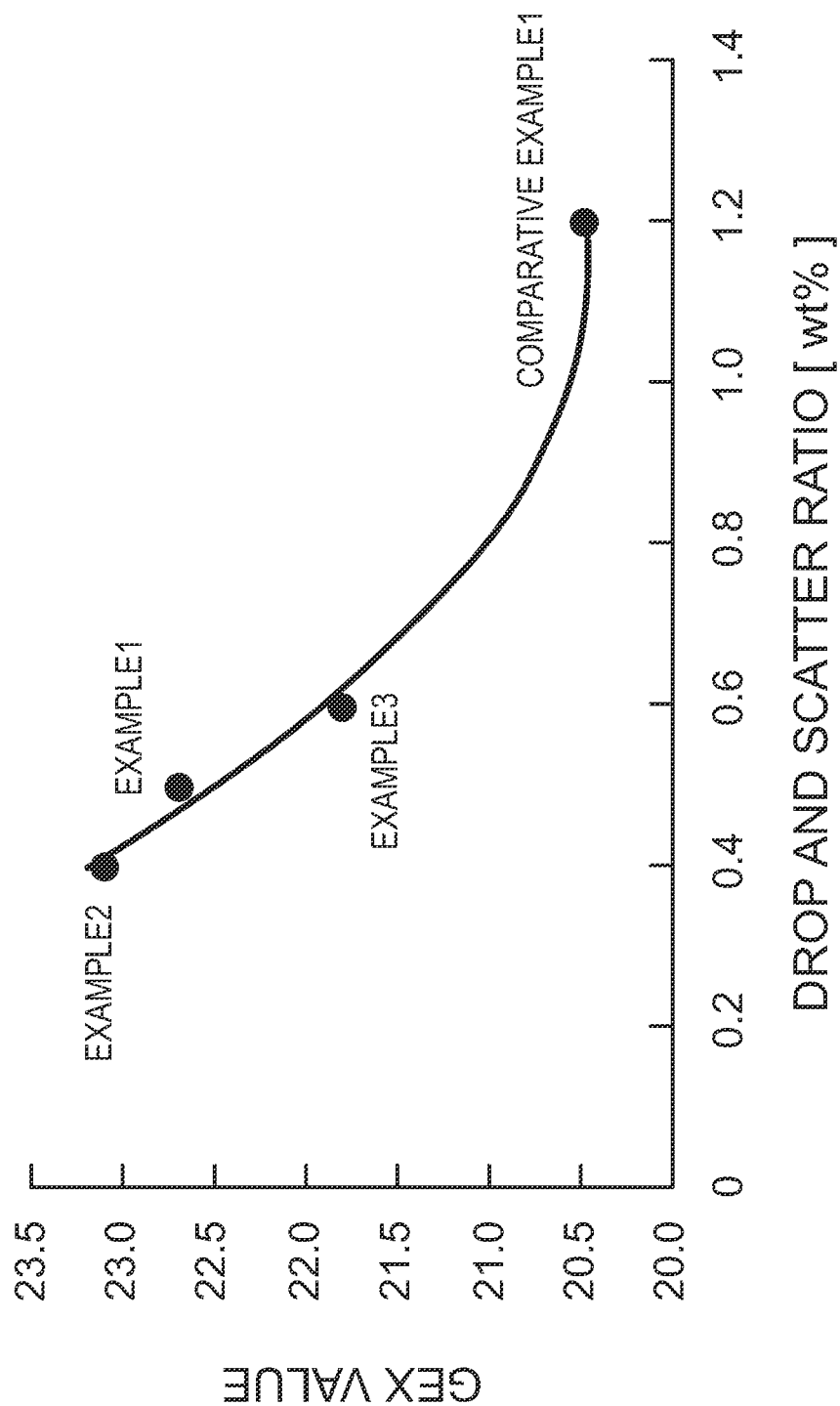

METHOD FOR PRODUCING WATER ABSORBENT RESIN

CROSS REFERENCE TO RELATED APPLICATIONS

This application is a National Stage of International Application No. PCT/JP2011/051003, filed on Jan. 20, 2011, which claims priority to Japanese Application No. 2010-009812 filed Jan. 20, 2010, Japanese Application No. 2010-055236, filed Mar. 12, 2010, and Japanese Application No. 2010-084024 filed Mar. 31, 2010. The content of the prior applications are incorporated herein by reference in their entirety.

TECHNICAL FIELD

The present invention relates to a method for producing a water absorbent resin. More specifically, it relates to improvement of a drying method for providing a water absorbent resin with high physical performance in high concentration polymerization (a polymerization method with a solid content concentration of 45% or more by weight, preferably of 50% or more by weight, and more preferably of 55% or more by weight).

BACKGROUND ART

A water absorbent resin (SAP/Super Absorbent Polymer) is a water swellable and water insoluble polymeric gellant, which is widely and mainly used in disposable articles including an absorbing article such as a disposable diaper, a sanitary napkin, an agricultural and horticultural water retaining agent, and an industrial water stopping agent. As a material for the water absorbent resin, varieties of monomers and hydrophilic polymers have been proposed. Among them, a polyacrylic acid (salt)-type water absorbent resin, which is formed by using acrylic acid and/or a salt thereof as a monomer, is widely used in industrial purposes due to its high water absorption performance.

The water absorbent resin can be obtained by micronizing a hydrogel polymer, which is obtained by polymerizing an aqueous monomer solution, either during or after polymerization, then, drying the particulate hydrogel polymer obtained (Non-Patent Literature 1).

As for the method of drying water absorbent resin, a method of using a belt type dryer (Patent Literatures 1 to 5), a method of thin film drying by using a drum dryer or the like (Patent Literature 6), a method for azeotropic dehydration in an organic solvent (Patent Literature 7), a method for drying in fluidized bed (Patent Literature 8), a method for drying in a bed fluidized by vibrating (Patent Literature 9), and a method for drying under stirring by using a rotor (Patent Literature 10), or the like are known.

As a condition for drying water absorbent resin, a method of controlling dew point or temperature (Patent Literatures 11 and 12) and a method of crushing during drying to dry under stirring (Patent Literature 13), or the like have been suggested for improving physical properties (for example, reducing residual monomers, increasing water absorption capacity, and reducing water extractable components).

Further, since non-dried products may occur during drying of a water absorbent resin to cause excessive load on crushing, a method for removing non-dried products is also known (Patent Literatures 14 to 16). To prevent occurrence of non-dried products, a method of regulating fluidity of a polymer gel (Patent Literature 17), a method of using a gel floating device in a dryer (Patent Literatures 18 and 19), a method of drying by using a specific apparatus for supplying constant quantity of a gel to a dryer (Patent Literature 20), a method of using infrared or the like in combination with hot air (Patent Literature 21) are known. Further, for improvement of drying efficiency, a method of adding a surfactant or an inorganic fine particle to hydrogel (Patent Literatures 22 to 26) is also known. A drying method for hydrogel with low neutralization rate is also known (Patent Literature 27). Still further, a method of drying at 100 to 250° C. with the content index of a thermally decomposable radical polymerization initiator at 40 to 100 in a hydrogel before drying is known (Patent Literature 28).

CITATION LIST

Patent Literature

Patent Literature 1: US Patent Application Publication No. 2008/214,749
Patent Literature 2: WO 2008/087114
Patent Literature 3: WO 2008/037676
Patent Literature 4: Japanese Patent Application Laid-Open (JP-A) No. 8-073518
Patent Literature 5: JP-A No. 7-270070
Patent Literature 6: JP-A No. 54-053165
Patent Literature 7: JP-A No. 57-198714
Patent Literature 8: U.S. Pat. No. 6,906,159
Patent Literature 9: JP-A No. 2001-018222
Patent Literature 10: U.S. Pat. No. 5,005,771
Patent Literature 11: U.S. Pat. No. 4,920,202
Patent Literature 12: U.S. Pat. No. 6,207,796
Patent Literature 13: U.S. Pat. No. 6,187,902
Patent Literature 14: U.S. Pat. No. 6,291,636
Patent Literature 15: U.S. Pat. No. 6,641,064
Patent Literature 16: WO 2007/057350
Patent Literature 17: US Patent Application Publication No. 2008/0,021,150
Patent Literature 18: JP-A No. 10-059534
Patent Literature 19: U.S. Pat. No. 5,229,487
Patent Literature 20: JP-A No. 2003-012812
Patent Literature 21: JP-A No. 2007-224224
Patent Literature 22: JP-A No. 2000-143720
Patent Literature 23: JP-A No. 2002-226599
Patent Literature 24: US Patent Application Publication No. 2007/123,624
Patent Literature 25: JP-A No. 2006-160774
Patent Literature 26: U.S. Pat. No. 5,945,495
Patent Literature 27: WO 2008/034786
Patent Literature 28: WO 2007/116778

Non Patent Literature

Non Patent Literature 1: The Modern Superabsorbent Polymer Technology (1998), p. 87 to 93, FIGS. 3, 6 and others.

SUMMARY OF INVENTION

Technical Problem

In recent years, production scale of a water absorbent resin gradually increases due to increasing demand for a disposable diaper or the like. There is also a tendency that scaling up per line or increasing the polymerization concentration (using an aqueous monomer solution of higher concentration or the like) is desired.

Accompanied by an increase in production scale, however, deterioration of physical properties or a trouble associated with scaling up also occurs often. For example, according to the drying step represented by Patent Literatures 1 to 13 described above, generation of non-dried products caused by scaling up or deterioration of physical properties due to excessive drying was observed. Removal of non-dried product (non-dried gel) disclosed in Patent Literatures 14 to 16 and others requires an additional step, thus it is accompanied with cost increase or complex plant operation. Use of other additives disclosed in Patent Literatures 22 to 26 and others may be also accompanied with deterioration of physical properties of a water absorbent resin caused by other additives (for example, lowered surface tension, lowered water absorption capacity under pressure, coloration, or the like) as well as cost increase. The method disclosed in Patent Literatures 17 to 21 also required an additional expensive device or a step for a dryer and the drying method of Patent Literature 27 is limited to a lowly neutralized water absorbent resin having neutralization rate of 55% by mole or less, and it may not be applied to a common water absorbent resin (for example, a resin with neutralization rate of 60 to 80% by mole). The drying method of Patent Literature 28 may also have a problem of coloration due to use of an increased amount of persulfate salt. In accordance with production amount increase of a water absorbent resin, increasing the concentration during polymerization, increasing the injection amount, or shortening the polymerization time or drying time have been tried under the purpose of improving productivity. However, such productivity improvement is generally associated with deterioration of physical properties of a water absorbent resin.

The above problem is particularly significant when a hydrogel having higher solid content concentration is dried (hydrogel crosslinked polymer after polymerization). In other words, although it is well known according to conventional production of a water absorbent resin that monomer concentration is increased to 20% by weight, 30% by weight, 40% by weight, or 50% by weight during polymerization for productivity improvement, cost reduction, and energy reduction during production step ($CO_2$ emission amount reduction) and others. However, there is a problem in general that physical properties or the like of the water absorbent resin to be obtained are greatly deteriorated (lowered water absorption capacity and increased water extractable content) when higher monomer concentration is used. Thus, it is clear that concentration increase during polymerization yields sacrifice of physical properties.

Accordingly, provided by the invention is a method for efficient drying of a water absorbent resin with the same or improved physical properties, which is used in a method for producing a water absorbent resin by drying particulate hydrogel having a high solid content concentration (45% by weight or more, preferably 50% by weight or more, and more preferably 55% by weight or more).

Solution to Problem

Inventors of the invention studied to solve the problems described above, and as a result found that, physical properties of a hydrogel after polymerization is not much lowered even when polymerization is carried out at high monomer concentration but a huge decrease in physical properties is resulted when such hydrogel with a high solid content concentration is dried. Specifically, the problem of deterioration of physical properties of a water absorbent resin depending on increased concentration during polymerization is mostly caused by deterioration of physical properties during drying with high concentration (deteriorated physical properties of a hydrogel after polymerization, in particular, water absorption capacity and extractables of a dried product, and below-described GEX value representing correlation between them) rather than deterioration of physical properties during high concentration polymerization (deterioration of physical properties of a hydrogel after drying, in particular, water absorption capacity and extractable of a dried product). It was also found that, when a hydrogel with a high solid content concentration (45% by weight or more and preferably 50% by weight or more) is subjected to air circulation drying, in particular drying by using a belt type dryer, under the same condition as a hydrogel with low solid content concentration (20 to 40% by weight), not only the deterioration of physical properties is caused but also drop of a dried gel from a through-circulation belt or scatter of a dried gel caused by dry air is significant so that yield reduction or a machine trouble occurs and the deterioration of physical properties resulting from uneven drying caused by such problems also becomes significant.

To solve the problems described above, the inventors earnestly studied. As a result, it was found that, for drying hydrogel having a high solid content concentration, the problems can be solved by controlling the drop and scatter ratio of particulate hydrogel crosslinked polymer from the through-circulation belt to be within a specific range.

That is, a method for producing a water absorbent resin according to the present invention (first method) is characterized by including: a polymerization step for polymerizing an unsaturated monomer; and a drying step for drying a particulate hydrogel crosslinked polymer having solid content concentration of 45% by weight or more, that is obtained by micronization of the hydrogel crosslinked polymer either during or after the polymerization, wherein a through-circulation belt type dryer is used for drying in the drying step and drop and scatter ratio of the particulate hydrogel crosslinked polymer that is represented by following Formula 1 is set to 1% by weight or less.

[Expression 1]

Drop and scatter ratio[% by weight]={1−(Amount of solid content in particulate hydrogel resulting from drying step/Amount of solid content in particulate hydrogel provided to through-circulation belt)}×100.  [Formula 1]

Further, a method for producing a water absorbent resin according to the present invention (second method) is characterized by including: a polymerization step for polymerizing an unsaturated monomer; and a drying step for drying a particulate hydrogel crosslinked polymer having solid content concentration of 45% by weight or more, that is obtained by micronization of the hydrogel crosslinked polymer either during or after the polymerization, wherein a through-circulation stationary batch type dryer equipped with a through-circulation plate is used for drying in the drying step and drop and scatter ratio of the particulate hydrogel crosslinked polymer, that is represented by following Formula 2, is set to 1% by weight or less.

[Expression 2]

Drop and scatter ratio[% by weight]={1−(Amount of solid content in particulate hydrogel resulting from drying step/Amount of solid content in particulate hydrogel provided to through-circulation plate)}×100.  [Formula 2]

Further, a method for producing a water absorbent resin according to the present invention (third method) is characterized by including: a polymerization step for polymerizing an unsaturated monomer; and a drying step for drying a particulate hydrogel crosslinked polymer having solid content concentration of 45% by weight or more, that is obtained by micronization of the hydrogel crosslinked polymer either during or after the polymerization, wherein a through-circulation belt type dryer is used for drying in the drying step and dropped residuals are periodically removed from the dryer.

Advantageous Effects of Invention

According to the invention, a water absorbent resin having maintained/improved physical properties (in particular, in terms of the relative relation between water absorption capacity and water extractable) can be efficiently obtained even when a water absorbent resin is produced by drying particulate hydrogel crosslinked polymer having a high solid content concentration (45% by weight or more, further 50% by weight or more, and particularly 55% by weight or more). Even when scaling up or increasing polymerization concentration (increasing solid content concentration) is performed, use of additives (surfactant) or a significant change in production apparatus like the conventional techniques described above is not really required, and the deterioration of physical properties, occurrence of uneven drying, or reduction in yield is inhibited, and therefore efficient drying can be achieved.

BRIEF DESCRIPTION OF DRAWINGS

FIG. 1 is a graph for illustrating the correlation between drop and scatter ratio and GEX value according to the invention.

BEST MODE FOR CARRYING OUT THE INVENTION

Herein below, the method for producing a water absorbent resin of the invention is described in greater detail, but the scope of the invention is not limited to this, and the invention may be altered in many variations as long as the range of the entity of the invention is not impaired. Specifically, the invention is not limited to the following embodiment, but may be altered in many variations within the scope of claims. That is, an embodiment based on a proper combination of technical method disclosed in different embodiments is encompassed in the technical scope of the invention.

[1] Definition of Terms (1-1) "Water Absorbent Resin"

"water absorbent resin" used herein is a water swellable and water insoluble polymer gellant. "water swellable property" indicates CRC (water absorption capacity without load) of the water absorbent resin, which is set forth in ERT 441.2-02, is essentially 5 g/g or more, preferably 10 to 100 g/g, and more preferably 20 to 80 g/g. "water insoluble property" indicates that Ext (water extractables) of a water absorbent resin, which are set forth in ERT 470.2-02, are essentially 0 to 50% by weight, preferably 0 to 30% by weight, still more preferably 0 to 20% by weight, and particularly preferably 0 to 10% by weight.

The water absorbent resin is not specifically limited, and it can be appropriately designed according to the use. Preferably, it is a hydrophilic crosslinked polymer obtained by crosslinking polymerization of an unsaturated monomer having a carboxy group. The water absorbent resin is not limited to an embodiment where whole amount (100%) is a polymer, and may include additives and the like, in an amount of the range to maintain the performance. Specifically, even a water absorbent resin composition is broadly referred to as a water absorbent resin in the invention. Content of the polyacrylic acid (salt)-type water absorbent resin is 70 to 99.9% by weight, more preferably 80 to 99.7% by weight, and still more preferably 90 to 99.5% by weight relative to the total amount. As components other than the water absorbent resin, in view of water absorbing speed or impact resistance of powders (particles), water is preferable and the additives to be described later are contained, as needed.

(1-2) "Polyacrylic Acid (Salt)"

In the present description, "polyacrylic acid (salt)" represents a polymer composed principally of acrylic acid and/or a salt thereof (herein below, referred to as acrylic acid (salt)) as a repeating unit in which a graft component is optionally included.

Specifically, it represents a polymer containing acrylic acid (salt) essentially in 50 to 100% by mole, preferably 70 to 100% by mole, more preferably 90 to 100% by mole, and particularly preferably substantially 100% by mole, in the entire monomers (excluding an internal crosslinking agent) used in polymerization. The salt as the polymer contains essentially a water soluble salt, when polyacrylic acid salt is used as a polymer. As a neutralization salt, the main component is preferably a monovalent salt, and further preferably an alkali metal salt or an ammonium salt, the alkali metal salt is more preferable, and further a sodium salt is particularly preferable.

(1-3) "EDANA" and "ERT"

"EDANA" is an abbreviation of European Disposables and Nonwovens Association, and "ERT" is an abbreviation of the measurement method (EDANA Recommended Test Methods) for the water absorbent resin of a European standard (nearly a world standard).

Meanwhile, in the present description, unless otherwise specified, the ERT original (which is a known literature revised in 2002) is referred to for measuring physical properties of the water absorbent resin.

(a) "CRC" (ERT 441.2-02)

"CRC" is an abbreviation of centrifuge retention capacity and it represents water absorption capacity without load (herein below also referred to as "water absorption capacity"). Specifically, it is a water absorption capacity (unit: [g/g]) at which 0.200 g of a water absorbent resin present in a non-woven fabric is allowed to be freely swollen in a large excess amount of a 0.9 wt % sodium chloride aqueous solution for 30 minutes and further drained by centrifugation.

(b) "AAP" (ERT 442.2-02)

"AAP" is an abbreviation of absorption against pressure and it means water absorption capacity with load. In detail, AAP is a water absorption capacity (unit: [g/g]) at which 0.900 g of a water absorbent resin placed under a pressure of 2.06 kPa (0.3 psi, 21 [g/cm$^2$]) is swollen in a 0.9% sodium chloride aqueous solution for an hour. In the invention, the measurement was made with changing the pressure condition including into a pressure of 4.83 kPa (0.7 psi, 50 [g/cm$^2$]) for one hour.

(c) "Ext" (ERT 470.2-02)

"EXT" is an abbreviation of extractables and represents extractables in water (quantity of water soluble contents). The extractables are of a value (unit; weight %) determined through steps of dissolving 1.000 g of a water absorbent resin in 200 g of a 0.9% by weight sodium chloride aqueous solution, stirring a mixture thereof for 16 hours, and measuring an amount of the polymer dissolved in the solution by pH titration.

(d) "FSC" (ERT 440.2-02)

"FSC" is an abbreviation of a free swell capacity. Specifically, FSC is a water absorption capacity (unit: [g/g]) at which 0.20 g of a water absorbent resin is immersed in a 0.9% by weight sodium chloride aqueous solution for 30 minutes, without draining is by centrifugation.

(e) "Residual Monomers (ERT 410.2-02)"

"Residual monomers" indicate an amount of monomers that are remained in a water absorbent resin. Specifically, it is an amount (unit: ppm) obtained by adding 1.0 g of a water absorbent resin to 200 mL of 0.9% by weight sodium chloride aqueous solution, stirring for 2 hours, and then measuring the amount of a residual monomer dissolved into the solution by high performance liquid chromatography.

(f) "PSD" (ETR 420.2-02)

"PSD" is an abbreviation of a particle size distribution and represents a particle size distribution determined by carrying out sieve classification. The weight average particle diameter (D50) and particle size distribution width are measured according to the same method as "(1) Median Particle Size and Distribution of Particle Size" described in lines 25 to 43 at page 7 of EP Patent No. 0349240.

(g) Measurement of Other Physical Properties of Water Absorbent Resin Set Forth in EDANA "pH" (ERT 400.2-02):

It represents pH of a water absorbent resin.

"Moisture Content" (ERT 430.2-2):

It represents a moisture content in a water absorbent resin.

"Flow Rate" (ERT 450.2-02):

It represents a flow rate of a water absorbent resin.

"Density" (ERT 460.2-02):

It represents a bulk density of a water absorbent resin.

"Respirable Particles" (ERT 480.2-02):

It represents water absorbent resin powder in breathable region.

"Dust" (ERT 490.2-02):

It represents powder dust contained in a water absorbent resin.

(1-4) "Liquid Permeability"

"liquid permeability" represents flow of liquid that flows among particles of water absorbent resin powder swelled with load or without load. A typical measurement method of "liquid permeability" includes SFC (Saline Flow Conductivity) or GBP (Gel Bed Permeability).

The phrase "SFC (Saline Flow Conductivity)" represents a liquid permeability of 0.69% by weight of sodium chloride aqueous solution for 0.9 g of a water absorbent resin powder with load of 0.3 psi. SFC is measured by SFC testing method described in the specification of U.S. Pat. No. 5,669,894.

The phrase "GBP" represents a liquid permeability of 0.69% by weight of sodium chloride aqueous solution for a water absorbent resin powder with load or in free expansion. GBP is measured by GBP testing method described in WO 2005/016393.

(1-5) "Color Hue"

In the invention, color hue of a water absorbent resin right after the production or color hue of a water absorbent resin right after the shipment to a user is referred to as initial color hue. In general, it is controlled for color hue before shipment from factory. Examples of the color hue measurement method include those described in WO 2009/005114 (for example, Lab values, YI values, WB values, and the like).

Change in color hue of a water absorbent resin which occurs during a long time storage or commercial distribution in unused state is referred to as color hue over time. Due to coloration of a water absorbent resin over time, product value of a disposable diaper may be lowered. The coloration over time occurs over several months to several years, and it is determined by acceleration test described in WO 2009/005114 (acceleration test under high temperature and high humidity).

(1-6) Others

The phrase "X to Y" indicating a range in the present specification represents "X or more and Y or less". The symbol "t (ton)" which is a unit of weight represents "Metric ton". The unit "ppm" represents "ppm by weight" or "ppm by mass" if not otherwise specified. In the present description "mass" and "weight", "% by mass" and "% by weight", and "parts by mass" and "parts by weight" have the same meaning as each other. Physical properties or the like are measured under the room temperature 20 to 25° C. and relative humidity of 40 to 50%, unless specifically described otherwise. The term "-acid (salt)" represents "-acid and/or a salt thereof", and the term "(meth)acryl" represents "acryl and/or methacryl".

[2] Method for Producing Water Absorbent Resin (2-1) Polymerization Step

This is a step for obtaining a crosslinked polymer in a hydrogel state (herein below, referred to as "hydrogel") by polymerization of an aqueous solution containing acrylic acid (salt) as a main component.

(a) Method for Producing Acrylic Acid

The method for producing acrylic acid, which is used as a raw material of the water absorbent resin provided by the invention, is not specifically limited. For example, the production method include a method of obtaining acrylic acid by vapor-phase oxidation of propylene or propane which is a fossil raw material and a method of obtaining acrylic acid by oxidation of glycerin or the like that is obtained from natural fats and oils as a non-fossil raw material. Such oxidations may be carried out via producing acrolein or may include isolating acrolein. Acrylic acid may be also obtained by direct oxidation.

Examples of method for producing a water absorbent resin by using acrylic acid derived from a non-fossil raw material are disclosed in, WO 2006/092272, WO 2006/136336, WO 2008/023040, WO 2007/109128, and the like. Also, examples of the method for preparing acrylic acid from a non-fossil raw material are disclosed in, WO 2006/087024, WO 2006/087023, WO 2007/119528, WO 2007/132926, US Patent Application Publication No. 2007/0129570, and the like.

(b) Impurities in Acrylic Acid

About the impurities contained in acrylic acid used in the invention, an amount of protoanemonin and/or furfural is preferably controlled so as to be a predetermined amount or less in consideration of a color hue stability or a residual monomer. The content thereof is preferably 0 to 10 ppm, more preferably 0 to 5 ppm, still more preferably 0 to 3 ppm, and particularly preferably 0 to 1 ppm.

For the same reason, it is preferable to include a smaller amount (s) of aldehydes other than furfural and/or maleic acid. An amount(s) thereof relative to acrylic acid is preferably 0 to 5 ppm, more preferably 0 to 3 ppm, still more preferably 0 to 1 ppm, and particularly preferably of 0 ppm (below the detection limit). Examples of aldehydes other than furfural encompass benzaldehyde, acraldehyde, acetaldehyde, and the like.

From the view point of reducing a residual monomer, acrylic acid includes dimer acrylate in amount preferably 0 to 500 ppm, more preferably 0 to 200 ppm, and still more preferably 0 to 100 ppm.

(c) Monomers (Excluding a Crosslinking Agent)

The water absorbent resin provided by the invention preferably contains, as a main component, acrylic acid (salt) as a raw material (monomer). In other words, according to the invention, it is preferable that the unsaturated monomer contains acrylic acid as a main component and the water absorbent resin is a water absorbent resin based on polyacrylic acid (salt). Polymerization of the monomer is generally carried out in an aqueous solution. A concentration of the monomer in the aqueous monomer solution is generally 10 to 90% by weight, preferably 20 to 80% by weight, more preferably 30 to 70% by weight, and still more preferably 40 to 60% by weight.

In the hydrogel obtained by polymerization of an aqueous solution, at least part of the acidic group of the polymer is preferably neutralized from the view point of water absorption performance. The neutralization may be carried out before, during, or after the polymerization of acrylic acid. From the view point of improving productivity, water absorption against pressure (AAP) and saline flow conductivity (SFC), or the like, it is preferable that the neutralization is carried out before the polymerization of acrylic acid. Specifically, neutralized acrylic acid (that is, partially neutralized acrylic acid salt) is preferably used as a monomer.

Neutralization rate is not specifically limited. However, relative to an acidic group, it is preferably 10 to 100% by mole, more preferably 30 to 95% by mole, still more preferably 50 to 90% by mole, and particularly preferably 60 to 80% by mole. When the neutralization rate is less than 10% by mole, CRC (water absorption capacity without load) or absorption speed may be lowered, in particular.

When an acrylic acid (salt) is used in the invention as a main component, a hydrophilic or hydrophobic unsaturated monomer other than the acrylic acid (salt) (herein below, also referred to as "other monomer") may be used. Examples of the other monomer usable in the invention, not specifically limited, encompass methacrylic acid, (anhydrous) maleic acid, 2-(meth)acrylamide-2-methylpropanesulfonic acid, (meth) acryloxy alkane sulfonic acid, N-vinyl-2-pyrrolidone, N-vinyl acetamide, (meth) acrylamide, N-isopropyl(meth)acrylamide, N,N-dimethyl(meth)acrylamide, 2-hydroxyethyl(meth)acrylate, methoxypolyethylene glycol(meth) acrylate, polyethylene glycol(meth)acrylate, stearyl acrylate, and salts thereof, or the like. When such other monomer is used, the using amount thereof is not specifically limited as long as the water absorption characteristics of the water absorbent resin are not impaired. Preferably, it is preferably 0 to 50% by weight, and more preferably 0 to 20% by weight relative to the total weight of the monomers.

(d) Neutralization Salt

The basic material used for neutralization of acrylic acid as a monomer or the polymer after polymerization (hydrogel) is not specifically limited, and preferred examples thereof include a monovalent basic material such as hydroxide of an alkali metal like sodium hydroxide, potassium hydroxide, and lithium hydroxide or a (hydrogen) carbonate salt like sodium (hydrogen) carbonate and potassium (hydrogen) carbonate. Sodium hydroxide is particularly preferable. The temperature or neutralization (neutralization temperature) is not specifically limited, but it is preferably 10 to 100° C., and more preferably 30 to 90° C. With regard to the conditions other than the condition for neutralization treatment described above or the like, conditions described in WO 2004/085496 or the like are preferably employed for the invention.

(e) Crosslinking Agent (Internal Crosslinking Agent)

In the invention, it is particularly preferable, in view of water absorption performance of the water absorbent resin obtained, to use a crosslinking agent (also referred to as an internal crosslinking agent). The internal crosslinking agent that can be used is not specifically limited, and examples thereof include a crosslinking agent which is polymerizable with acrylic acid, a crosslinking agent which is reactive to a carboxyl group, and a crosslinking agent including both of them, or the like. Specific examples of the polymerizable crosslinking agent encompass a compound having at least two polymerizable double bonds within a molecule, such as N,N'-methylene bisacrylamide, (poly)ethylene glycol di(meth)acrylate, (polyoxyethylene)trimethylol propane tri (meth)acrylate, and poly(meth)allyloxyalkane. Examples of the reactive crosslinking agent encompass: a covalent crosslinking agent such as polyglycidyl ether such as ethylene glycol diglycidyl ether, polyalcohol such as propanediol, glycerin, sorbitol; and an ionic bonding crosslinking agent, which is a polyvalent metal compound such as aluminum. Of these, in view of a water absorption performance, it is preferable to use the crosslinking agent which is polymerizable with acrylic acid. Particularly, it is preferable to use an acrylate-type polymerizable crosslinking agent, an allyl-type polymerizable crosslinking agent, and an acrylamide-type polymerizable crosslinking agent. The internal crosslinking agent may be used either singly or in combination of two or more. In consideration of physical properties, the using amount of the internal crosslinking agent relative to the monomer excluding the crosslinking agent is preferably 0.001 to 5% by mole, more preferably 0.005 to 2% by mole, still more preferably 0.01 to 1% by mole, and particularly preferably 0.03 to 0.5% by mole.

(f) Methoxy Phenols

According to the invention, from the view point of polymerization stability, methoxy phenols are preferably contained in the monomer. More preferably, p-methoxy phenol is contained therein. The content of the methoxy phenols is preferably 1 to 250 ppm, more preferably 5 to 200 ppm, still more preferably 10 to 160 ppm, and particularly preferably 20 to 100 ppm relative to the monomer (acrylic acid).

(g) Iron Component

In the invention, from the view point of coloration and polymerization rate of the water absorbent resin, it is preferable that iron ion is contained as iron component in the monomer or the aqueous solution of the monomer. Content of the iron ion is, in terms of $Fe_2O_3$, preferably 0 to 10 ppm, more preferably 0 to 5 ppm, still more preferably greater than 0 but less than 5 ppm, further still more preferably 0.001 ppm or more and less than 5 ppm, particularly preferably 0.001 to 4 ppm, and most preferably 0.005 to 3 ppm relative to the monomer. The content of iron ion can be controlled according to the method described in WO 2006/109842. The expression "in terms of $Fe_2O_3$" represents the correction of measured Fe (molecular weight: 55.845) into $Fe_2O_3$ (molecular weight: 159.69), irrespective of the counter ions for Fe.

When the content of iron ion is not within the range described above, there is a possibility that coloration of the water absorbent resin occurs. Also, in the case where the content of iron ion is set to N. D (the detection limit or less, 0 ppm), there is a risk that causes an increase in cost, yielding the effect not worth the cost, and slowing down a polymerization rate in a case of a redox polymerization or the like.

Meanwhile, the amount of iron in the water absorbent resin can be measured, for example, by an ICP emission spectrophotometry method set forth in JIS K1200-6. Regarding an ICP emission spectrophotometry instrument, ULTIMA manufactured by Horiba, Ltd. and the like are commercially available.

(h) Other Components in Aqueous Solution of Monomer

In order to improve various physical properties of the water absorbent resin obtained by the invention, the following materials can be added as an optional component to the aqueous solution of a monomer. Specifically, starch or a water soluble resin or water absorbent resin such as polyacrylic acids (salt), polyvinyl alcohol, and polyethylene imine and others may be added in an amount of 0 to 50% by weight, preferably 0 to 20% by weight, more preferably 0 to 10% by weight, and still more preferably 0 to 3% by weight relative to the monomer. Additive such as various foaming agents (carbonate salt, azo compound, air bubbles, or the like), a surfactant, various chelating agents, hydroxy carboxylic acid, or a reductive inorganic salt may be added in an amount of 0 to 5% by weight, and preferably 0 to 1% by weight relative to the monomer, for example.

Among them, when preventing coloration of the water absorbent resin over time or improving urine resistance (preventing gel deterioration) is desired, chelating agent, hydroxy carboxylic acid, or reductive inorganic salt is preferably used. The chelating agent is particularly preferably used. The using amount for such case is preferably 10 to 5000 ppm, more preferably 10 to 1000 ppm, still more preferably 50 to 1000 ppm, and particularly preferably 100 to 1000 ppm relative to the water absorbent resin. As for the chelating agent, hydroxy carboxylic acid, or reductive inorganic salt, the compounds described in WO 2009/005114, EP Patent No. 2 057 228, or EP Patent No. 1 848 758 can be used.

(i) Polymerization Initiator

A polymerization initiator for use in the invention is selected as needed in accordance with the polymerization type, and not specifically limited. Examples of the polymerization initiator encompass a thermally degradable polymerization initiator, a photodegradable polymerization initiator, and a redox-type polymerization initiator, or the like. Specific examples of the thermally degradable polymerization initiator encompass persulfate such as sodium persulfate, potassium persulfate, or ammonium persulfate; and, peroxide such as hydrogen peroxide, t-butyl peroxide, or methyl ethyl ketone peroxide; and azo compound such as 2,2'-azobis(2-amidino-propane)dihydrochloride, 2.2'-azobis[2-(2-imidazolin-2-yl)propane]dihydrochloride, or the like. Specific examples of the photodegradable polymerization initiator encompass benzoin derivative, benzyl derivative, acetophenone derivative, benzophenone derivative, and azo compound, or the like. An example of the redox-type polymerization initiator encompasses use of a reducing compound such as L-ascorbic acid or sodium hydrogen sulfite in combination with persulfate or peroxide described above. A preferable example encompasses use of the photodegradable polymerization initiator in combination with the thermally degradable polymerization initiator described above. An using amount of the polymerization initiator is preferably 0.0001 to 1% by mole and more preferably 0.001 to 0.5% by mole relative to the monomer. When the using amount of the polymerization initiator is more than 1% by mole, the coloration of the water absorbent resin may occur. Whereas, when the using amount of the polymerization initiator is less than 0.0001% by mole, it may cause an increase in a residual monomer.

Meanwhile, it should be noted that, instead of using the above-described polymerization initiator, the monomer may be polymerized by irradiation of activated energy rays such as radiation rays, electron beams, and UV rays. Further, the polymerization may be carried out by the use of the polymerization initiator in combination with the activated energy rays.

(j) Polymerization Method

According to the invention, in consideration of water absorption performance of the water absorbent resin obtained or an easiness of control of polymerization, or the like, when polymerizing an aqueous solution of a monomer, the polymerization step is generally carried out by aqueous polymerization or reverse phase suspension polymerization. Particularly, the aqueous polymerization is used. More preferably, continuous aqueous polymerization is used. In particular, it is preferably used for huge scale production which allows a great production amount of the water absorbent resin per line. The production amount is preferably 0.5 [t/hr] or more, more preferably 1 [t/hr] or more, still more preferably 5 [t/hr] or more, and particularly preferably 10 [t/hr] or more. Further, preferred examples of the aqueous solution polymerization encompass continuous belt polymerization (disclosed in U.S. Pat. Nos. 4,893,999, 6,241,928, and US Patent Application Publication No. 2005/215,734 and others), continuous kneader polymerization, and batch kneader polymerization (disclosed in U.S. Pat. Nos. 6,987,151 and 6,710,141 and others) and others. Of these, the continuous kneader polymerization or continuous belt polymerization which allow water vaporization (particularly, solid components are increased by 1% by weight or more) are preferable. The continuous belt polymerization is particularly preferable.

Preferable example of the continuous aqueous polymerization encompasses high-temperature-starting polymerization, in which the polymerization initiation temperature is preferably 30° C. or more, more preferably 35° C. or more, still more preferably 40° C. or more, and particularly preferably 50° C. or more (an upper limit of the temperature of the monomer is a boiling point), and high-monomer-concentration-using polymerization, in which the concentration of monomer is preferably 35% by weight or more, more preferably 40% by weight or more, still more preferably 45% by weight or more (an upper limit of the concentration of the monomer is a saturated concentration). The polymerization initiation temperature is defined as the temperature of the liquid right before supplying the aqueous solution of a monomer to a polymerization reactor. However, the conditions and others described in U.S. Pat. Nos. 6,906,159, 7,091,253, or the like may be suitably applied for the invention.

Further according to the invention, from the viewpoint of improving the physical properties and drying efficiency of the water absorbent resin obtained in the invention, moisture is preferably vaporized during the polymerization. In other words, it is preferred in the polymerization of the invention that a hydrogel with high concentration of solid content is obtained. The level of increased solid content concentration ("concentration of a solid content in the hydrogel after polymerization"–"concentration of monomer before polymerization") is preferably 1% by weight or more, more preferably 2 to 40% by weight, and still more preferably 3 to 30% by weight. In this regard, the solid content concentration in the hydrogel obtained is preferably 80% by weight or less.

These polymerizations can be carried out in an air atmosphere. However, in view of the prevention of the coloration, it is preferable to carryout the polymerization in an inert gas atmosphere such as nitrogen or argon (for example, oxygen concentration is 1% by volume or less), and to polymerize a monomer component after replacing, by an inert gas, oxygen dissolved in the solution containing the monomer (for example, the dissolved oxygen concentration less than 1 [mg/L]). It may be carried out under reduced pressure, atmospheric pressure, or increased pressure. If necessary, the hydrogel obtained after the polymerization may be stored (aged) for reducing the residual monomers or controlling the recycle time for continuous production, or the like, after discharged from the polymerization reactor.

(2-2) Gel Micronization Step (Gel Crushing Step)

This is a step of crushing the hydrogel obtained from the polymerization step described above and followed by storing (aging) as required, to obtain particulate hydrogel (herein below, referred to as "particulate hydrogel").

The hydrogel obtained from the above polymerization step may be subjected to drying as it is. However, to solve the problems, the hydrogel may be gel-crushed preferably during or after the polymerization by using a crushing machine (kneader, meat chopper, cutter mill, or the like) as needed to yield particulates. Specifically, between the polymerization step using continuous belt polymerization or continuous kneader polymerization and the drying step, the hydrogel micronization step (herein below, also referred to as "gel crushing") may be further included. Even when the gel is micronized by dispersion in a solvent during polymerization such as reverse phase suspension polymerization, that case is regarded to be encompassed by the micronization (micronization of the polymerization step) of the invention. However, it is preferably crushed by using a crushing machine.

In view of physical properties, temperature of the hydrogel to be crushed is kept or heated preferably 40 to 95° C. and more preferably 50 to 80° C. A resin solid content (solid content concentration) of the particulate hydrogel either during or after the gel crushing is not particularly limited. However, in view of the physical properties, it is preferably 45% by weight or more, more preferably 45 to 80% by weight, and still more preferably 55 to 80% by weight. The range described in the following section (2-3) is preferable. Under the purpose of enhancing the crushing efficiency, when required, water, polyhydric alcohol, a mixture solution of water and polyhydric alcohol, an aqueous solution of polyvalent metal, vapors thereof, or the like may be added during the gel crushing step. When the hydrogel having high solid content concentration (for example, 45 to 80% by weight as described above) to which the invention can be preferably applied is crushed, the inside of a crushing machine can be circulated with air, preferably with dry air.

The weight average particle diameter (D50) of the particulate hydrogel after gel crushing is preferably 0.2 to 4 mm, more preferably 0.3 to 3 mm, and still more preferably 0.5 to 2 mm from the view point of controlling the drop and scatter ratio at low level. By controlling the weight average particle diameter (D50) of the particulate hydrogel within the range described above, the drying is efficiently carried out, and therefore desirable. The ratio of the particulate hydrogel having a particle size of 5 mm or more is preferably 0 to 10% by weight, and more preferably 0 to 5% by weight relative to the entire particulate hydrogel.

Meanwhile, the particle size of the particulate hydrogel is obtained by classifying with a sieve with a specific hole size, similar to the particle size of the water absorbent resin after the crushing step. The weight average particle diameter (D50) can be obtained in a same manner. However, when dry-type classifying operation of the particulate hydrogel is difficult to achieve due to aggregation or the like, the wet classifying method described in paragraph [0091] of JP-A No. 2000-63527 can be used for the measurement.

(2-3) Drying Step

The invention is characterized by the drying step as described below. Specifically, according to the invention, a method for efficient drying of a water absorbent resin without having coloration, unevenness in drying, or reduction in yield while maintaining and improving the physical property is provided in relation to a method of producing a water absorbent resin by drying particulate hydrogel with high solid content concentration (45% by weight or more, preferably 50% by weight or more, and more preferably 55% by weight or more), in which the problems described above can be solved by controlling the drop and scatter ratio at 1% by weight or less.

Herein, the solid content concentration in particulate hydrogel is 45% by weight or more, 50% by weight or more, 55% by weight or more, and 60% by weight or more, and it is preferable in this order. The upper limit is, although not specifically limited as long as it is a hydrogel, 80% by weight or less, further 75% by weight or less, and particularly 70% by weight or less from the view point of lowering the residual monomers or the like. Meanwhile, the solid content concentration in a particulate hydrogel to be dried may be appropriately selected within the upper and lower ranges described above, depending on physical properties, productivity, or the like that is desired. For example, a range which is 45 to 80% by weight, 45 to 75% by weight, 50 to 75% by weight, 50 to 70% by weight, 55 to 80% by weight, 55 to 70% by weight, or 60 to 70% by weight or the like may be selected, and it is preferable in this order. When the solid content concentration is less than 45% by weight, not only the productivity is low but also the characteristic effect of the invention is not easily exhibited. On the other hand, when the solid content concentration is excessively high, physical properties such as water absorption capacity, extractables, and GEX value may be impaired. The solid content concentration is determined depending on the concentration of monomer during polymerization or vaporization during polymerization as well as the additives that are added either during or after the polymerization as required. However, the solid content concentration may be also controlled by adding the water absorbent resin powder or a hydrogel thereof as an additive. Specifically, it is preferable that the solid content concentration of the particulate hydrogel is increased by vaporization of moisture during the polymerization step or addition of the water absorbent resin powder or a hydrate thereof. Addition of the water absorbent resin powder (in particular, powder not added with any water) to a hydrogel either during or after the polymerization is preferable in that the solid content concentration before drying is increased, fluidity of the gel during drying is improved, and also the releasing property from a belt after drying is improved.

The invention is characterized in that the drop and scatter ratio described above is maintained at low level for the drying of a hydrogel having high solid content concentration. For controlling the drop and scatter ratio, (a) a dryer, (c) thickness of a hydrogel, and (d) area occupancy ratio are preferably used as described below. Herein below, preferable drying methods are described.

(a) Dryer

A dryer used in the invention is a through-circulation dryer (also referred to as an "air circulation type dryer"). The through-circulation dryer includes a continuous through-circulation dryer in which a product to be dried is dried by hot air while it is transported through the inside of a dryer as loaded on a through-circulation belt and a stationary type (batch type) in which a product to be dried is loaded on a through-circulation plate and then it is dried by hot air while the through-circulation plate is kept at stationary state, and each is also referred to as a through-circulation belt type dryer and a through-circulation stationary batch type dryer, respectively. Meanwhile, the through-circulation belt type dryer is also referred to as a "band type continuous through-circulation dryer", or the like. According to the invention, from the view point of compatibility with continuous polymerization, efficient drying at large scale, and physical properties of a water absorbent resin, it is preferable to use a through-circulation belt type dryer as a through-circulation dryer.

Meanwhile, for an industrial scale test (for setting drying condition) using a through-circulation continuous type dryer such as a through-circulation belt type dryer, continuous drying at large scale (in particular, 0.5 [t/hr] or more, further 1 [t/hr] or more, or 5 [t/hr] or more) and production for several hours to several days is generally required. However, since the physical properties of a water absorbent resin that is obtained by setting the drying condition at constant level represents almost the same behavior between continuous drying and batch type drying, the batch type drying can be employed in view of a simulation test of continuous drying. Specifically, a drying test is carried out at small scale as a model test of continuous drying (several kg to several tens of kg per batch), and operation conditions of a through-circulation belt type dryer can be determined while confirming the correlation between continuous drying at large scale and batch drying at small scale. For example, the drying condition for a through-circulation stationary batch type dryer of Examples 1 to 3 (described below) may be also employed as it is for the drying step of a through-circulation belt type dryer. Accordingly, based on the results of drying obtained from a through-circulation stationary batch type dryer, drying conditions of a through-circulation belt type dryer is set, and therefore drying amount per unit hour can be easily scaled up by 10 times or more, 100 times or more, or 200 to 10,000 times.

Herein below, a through-circulation dryer is described in greater detail. However, the invention is not limited to the following examples.

Size or the like of a through-circulation dryer used in the invention is not specifically limited. When the through-circulation dryer is a through-circulation belt type dryer, a large scale through-circulation belt type dryer having a through-circulation belt length in the range of 5 to 100 m, further 10 to 70 m, and particularly 20 to 60 m is preferable. The invention is particularly suitable for a large scale continuous drying using such through-circulation belt type dryer. For such case, the width of a through-circulation belt is, although not specifically limited, properly determined within the range of typically 0.5 to 10 m, and further 1 to 5 m. Meanwhile, ratio between the width direction and the length direction can be determined depending on purpose. However, it is longer in the moving direction compared to the width direction, and appropriately determined in typically 3 to 500 times and further 5 to 100 times. Further, when continuous drying is performed, the continuous operation time is not specifically limited, and it can be appropriately determined, for example, 10 hours to 10 years, 1 day to 5 years, or 10 days to 1 year, or the like.

According to the invention, drying is carried out on a through-circulation belt when a through-circulation belt type dryer is used. When a through-circulation stationary batch type dryer is used, it is performed on a through-circulation plate. As a material for constituting a through-circulation belt or a through-circulation plate, a wire mesh (for example, sieve hole size of 1000 to 45 µm) or a punching metal (punching plate) is exemplified. Preferably, a punching metal is used. Examples of the shape of the hole of a punching metal can be broadly applied, and examples thereof include a round hole, an oval hole, a rectangular hole, a hexagonal hole, a long and round hole, along rectangular hole, a diamond-shape hole, a cross-shape hole, and a combination thereof. The hole arrangement may be either a staggered shape or a parallel shape. Further, the holes may be formed in three dimensions such as a louver (a bay window). Preferably, however, it has a hole in plane structure. Further, the pitch direction may be either vertical or horizontal to the moving direction of the belt. It may be also either tilted or combination of any directions. Meanwhile, the hole size and the hole area ratio of a punching metal are described below.

When a through-circulation belt type dryer is used, the transport speed of a particulate hydrogel on a through-circulation belt can be appropriately adjusted according to the belt width, belt length, production amount, and drying time for controlling the drop and scatter ratio at low rate. However, from the view point of loading on a belt driving apparatus and durability or the like, it is preferably 0.3 to 5 [m/min], more preferably 0.5 to 2.5 [m/min], still more preferably 0.5 to 2 [m/min], and particularly preferably 0.7 to 1.5 [m/min]. When the speed is too fast, not only the durability is lowered but also vibration of an apparatus is increased, yielding higher drop and scatter ratio.

In order to achieve the purpose of the invention, temperature, dew point, and an air flow amount in the dryer, are preferably changed in multi steps. For such reasons, when a through-circulation belt type dryer is used, the through-circulation belt type dryer preferably has a multi-chamber structure. In particular, the dryer is preferably a through-circulation belt type dryer having 5 or more chambers, particularly 6 or more chambers, and further 8 or more chambers. The upper limit is appropriately set depending on a scale or the like. In general, 20 chambers or so are sufficient.

(b) Definition of Thickness (Thickness Change Ratio) of Hydrogel

When a through-circulation belt type dryer is used in the invention, thickness and state of a particulate hydrogel that is loaded on a through-circulation belt are not specifically limited. However, from the view point of even drying and maintaining physical properties, drying on a through-circulation belt while having a change in thickness direction is preferred compared to even thickness. Specifically, the thickness change ratio (1) in width direction of a hydrogel, which is defined by the Formula 3 below, is preferably from 1.05 to 5.00. Further, the thickness change ratio (2) in width direction of a hydrogel, which is defined by the Formula 4 below, is preferably from 1.05 to 3.00.

[Expression 3]

Thickness change ratio(1)=Maximum thickness of hydrogel in width direction of through-circulation belt/Average thickness of hydrogel in width direction of through-circulation belt  [Formula 3]

[Expression 4]

Thickness change ratio(2)=Maximum thickness of hydrogel at both ends of through-circulation belt/Maximum thickness of hydrogel at center of through-circulation belt  [Formula 4]

In the above Formula 3, the term "thickness in width direction" represents the thickness at cross-section of the hydrogel in the perpendicular plane relative to the moving direction of a continuously operated through-circulation belt, at the point where the hydrogel is loaded completely. It can be measured by, for instance, using a laser type trip meter or a laser type displacement meter, or the like. Meanwhile, the term "thickness of hydrogel" does not mean the thickness of one hydrogel grain. Instead, it means a thickness as a group resulting from stacking of a hydrogel particle. The term "maximum thickness in width direction" represents the maximum value obtained by measuring thickness in width direction either continuously or every 10 cm from the center of a through-circulation belt (for example, 21 spots at maximum for a through-circulation belt with width of 2 m). Further, the term "average thickness in width direction" represents the average value obtained by measuring thickness in width direction either continuously or every 10 cm from the center of a through-circulation belt (for example, 21 spots at maximum for a through-circulation belt with width of 2 m).

Further, in the above Formula 4, the term "both ends of through-circulation belt" represents a part having a width that is ⅓ of the entire width of a through-circulation belt, from each of the two ends of a through-circulation belt. Further, the term "maximum thickness at both ends" represents the maximum value when measured at the position at which the height is the biggest for both ends (⅓ in the left and right). The maximum value may be found at any of the two ends. Further, the term "the center of the through-circulation belt" represents a part other than the both ends described above. The term "the maximum thickness at the center of the through-circulation belt" represents the maximum value when measured at the position at which the height is the biggest in center part (⅓ in the center).

Thickness change of a hydrogel more preferably varies in symmetric manner from the center point in width direction of a through-circulation belt toward the two ends. Further, the "maximum thickness at both ends" is more preferably present at least one of two parts in which the width is ⅙ of the entire width of a through-circulation belt.

(c) Thickness of Hydrogel (Thickness of Laminar of Particulate Hydrogel)

For improving physical properties of water absorption capacity or extractables, or the like in a method for polymerizing a water absorbent resin, a method of controlling the polymerized gel thickness in width direction of a horizontal belt at constant level has been conventionally known (U.S. Pat. No. 6,241,928). Further, to control the gel thickness during through-circulation belt drying at constant level, a drying method using a gel leveling machine such as a roller in a dryer is also known (Patent Literature 17). There is also a method that a gel is transported by using a roller on a through-circulation belt type dryer (Patent Literatures 4 and 5).

According to conventional techniques, as a hydrogel having low solid content concentration is dried, in particular, improving physical properties or reducing the production amount of a non-dried product by controlling the thickness of a hydrogel, that is, thickness of a particulate hydrogel laminar, at even and constant level is suggested.

However, it was found that, when a hydrogel having high solid content concentration, in particular, a hydrogel with solid content concentration in the range described above, is dried and thickness of a particulate hydrogel laminar is controlled at even level, it is difficult to obtain the desired physical properties with high productivity, since the drying efficiency (amount of an non-dried product, yield of a dried product, or the like) and physical properties of an absorbent resin (CRC, extractables, residual monomers, color of a dried product, AAP, SFC, or the like) contradict each other.

In the invention, the thickness change ratio (1) described above is preferably 1.05 to 5.00. Lower limit of the thickness change ratio (1) is preferably 1.10 or more, more preferably 1.15 or more, still more preferably 1.20 or more, particularly preferably 1.25 or more, and most preferably 1.30 or more. The upper limit is preferably 2.00 or less, more preferably 1.80 or less, still more preferably 1.60 or less, and particularly preferably 1.50 or less. Numerical range of the thickness change ratio (1) is preferably 1.10 to 3.00, more preferably 1.15 to 2.00, still more preferably 1.20 to 1.80, particularly preferably 1.25 to 1.60, and most preferably 1.30 to 1.50.

In the invention, the thickness change ratio (2) described above is preferably 1.05 to 3.00. Lower limit of the thickness change ratio (2) is preferably 1.10 or more, more preferably 1.15 or more, still more preferably 1.20 or more, particularly preferably 1.25 or more, and most preferably 1.30 or more. The upper limit is 3.00 or less, preferably 2.00 or less, more preferably 1.80 or less, still more preferably 1.60 or less, and particularly preferably 1.50 or less. Numerical range of the thickness change ratio (2) is preferably 1.10 to 3.00, more preferably 1.15 to 2.00, still more preferably 1.20 to 1.80, particularly preferably 1.25 to 1.60, and most preferably 1.30 to 1.50.

In the invention, the thickness of a through-circulation belt in moving direction may be constant or changed periodically or non-periodically. When the thickness is changed in moving direction, the pattern (shape) or period is not specifically limited. Further, when thickness is changed in moving direction, the thickness change ratios (1) and (2) in width direction described above are defined by their average value. Thus, within a certain constant range, the thickness change ratios (1) and (2) may be microscopically out of the range described above. However, it is just required that the thickness change ratios (1) and (2) over the entire through-circulation belt are within the range described above. Specifically, the region in which the thickness change ratios (1) and (2) are included in the range described above is preferably 60% or more, more preferably 75%, still more preferably 90% or more, and particularly preferably 100% relative to the entire through-circulation belt.

Further, the average thickness value of a hydrogel that is loaded on a through-circulation belt or a through-circulation plate is typically 1 to 30 cm, preferably 2 to 20 cm, more preferably 5 to 15 cm, and still more preferably 7 to 13 cm. Further, the thickness of a hydrogel that is loaded on a through-circulation belt or a through-circulation plate is typically 0 to 30 cm, preferably 5 to 20 cm, more preferably 8 to 15 cm, and still more preferably 9 to 11 cm. When a through-circulation belt type dryer is used, in particular, drying efficiency or various physical properties of a water absorbent resin can be improved by controlling the average thickness value of a hydrogel or the thickness of a hydrogel to be within the range described above, and the bulk density of a water absorbent resin can be adjusted to high level, in particular.

(d) Area Occupancy Ratio

In the description, the term "area occupancy ratio" represents the ratio (percentage) of the area occupied by a hydrogel before drying, which is loaded on a through-circulation belt, in a through-circulation belt relative to the area of a through-circulation belt, when a through-circulation belt type dryer is used as a through-circulation dryer. Specifically, it is defined by area of a through-circulation belt from the point at which a hydrogel is placed on the through-circulation belt completely, to the point after moving in moving direction for 1 min, preferably 0.5 min, and most preferably 0.1 min. The area is appropriately determined by speed of a through-circulation belt. For example, when the through-circulation belt speed is 1 [m/min], it is an area from the point at which a hydrogel is placed on the through-circulation belt completely, to the point of 1 m, preferably 0.5 m, and most preferably 0.1 m. When the area of the through-circulation belt is (A) and the area occupied by a hydrogel loaded on the area is (B), the area occupancy ratio is represented by B/A×100[%].

Meanwhile, the point at which a hydrogel is placed on the through-circulation belt completely, represents the point of the end of hydrogel loaded in the moving direction, when observing the hydrogel from the direction of width, for example, the point is determined as the tip of the hydrogel spread in an arc shape or a wave shape.

For the drying step of the invention, the area occupancy ratio is preferably 85 to 100%, more preferably 87 to 100%, still more preferably 87 to 99%, particularly preferably 90 to 98%, and most preferably 93 to 97%. When the area occupancy ratio is out of the range above, the physical properties of a water absorbent resin may be impaired or drying efficiency may be lowered. The area occupancy ratio of less than 100% represents that a hydrogel is not loaded on at least part of a through-circulation belt. The region not loaded with a hydrogel may be any region of a through-circulation belt, but it is preferable that a certain region not loaded with a hydrogel is present at both ends of a through-circulation belt.

Based on the same effects and reasons described above, width occupancy ratio of a hydrogel loaded on a through-circulation belt is preferably 85 to 100%, more preferably 87 to 100%, still more preferably 87 to 99%, particularly preferably 90 to 98%, and most preferably 93 to 97% during the drying step using a through-circulation belt type dryer. In the present description, the term "width occupancy ratio" represents the ratio (percentage) of a width of a hydrogel before drying, which is loaded on a through-circulation belt, in a through-circulation belt relative to the cross section of a through-circulation belt. Specifically, it is defined by occupancy ratio of a hydrogel in width direction of a through-circulation belt at the point at which loading of a hydrogel on a through-circulation belt is terminated. Herein, the area occupancy ratio and the width occupancy ratio are substantially in the same range when averaged over a broad range, and therefore are interchangeable with each other.

Further, when a through-circulation belt type dryer is used and the occupancy area or occupancy width of a hydrogel on a through-circulation belt is periodically changed (for example, exhibiting wave shape in moving direction), the area occupancy ratio or the width occupancy ratio is evaluated by average value in the period. Thus, in period or partial region having a change, a case in which area occupancy ratio or width occupancy ratio is out of the range described above may be included. However, it is needless to say that, over the entire period on the through-circulation belt, the area occupancy ratio preferably falls within the range described above. Specifically, over a single period or a continuous drying period, the region having the area occupancy ratio or width occupancy ratio within the range above is preferably 60% or more, more preferably 75%, still more preferably 90% or more, and particularly preferably 100% relative to the entire through-circulation belt. In other words, it is preferable that the average area and/or the width occupancy ratio during a single period or a continuous drying period satisfy the range described above.

(e) Hole Area Rate and Hole

In the invention, hole area rate is defined by rate (percentage %) of hole area in a punching metal or a metal mesh relative to the entire area of the surface of the through-circulation belt surface or the through-circulation plate (including hole area). In order to control the drop and scatter ratio at low level, the hole area rate is 15 to 50%, more preferably 20 to 45%, and particularly preferably 25 to 40%. As used herein, the hole area rate is determined by hole, pitch (P), or the like, and it is defined by an area including an edge part, if no hole is included in certain area, that is, a punching metal has an edge part. When the hole area rate is not within the range described above, it was found that not only the drop and scatter ratio is lowered but also physical properties of a water absorbent resin are impaired. Further, the drying efficiency or continuous drying property in a case where a through-circulation belt type dryer is used tends to be lowered.

The hole included in a punching metal of a through-circulation belt of the invention preferably has the specific size described below.

Area of one hole (for a case of holes with multiple types, average opening area is defined as an average area) is preferably larger than a cross section area of one grain of a particulate hydrogel, and it is 2 to 100 times, or further 4 to 50 times. Further, the maximum opening distance of a hole (for example, diameter for a circle, or a large diameter for an oval) is preferably larger than the weight average particle diameter of a particulate hydrogel, and 2 to 100 times or further 4 to 50 times. In addition, the average opening area of a hole is 5 to 500 mm$^2$, preferably 10 to 10 mm$^2$, and particularly preferably 15 to 50 mm$^2$. If the area is smaller than the range defined above, drying efficiency is reduced. On the other hand, when it is bigger than the range defined above, the drop and scatter ratio of a dried product is increased, and therefore undesirable.

Further, it is preferable that at least part of the particulate hydrogel, further 1 to 50% by weight of the particulate hydrogel is smaller than the hole. Meanwhile, a technique of drying a hydrogel (for example, 1 to 2 mm) on a wire mesh (for example, sieve hole size of 300 μm) is conventionally known. However, the invention is characterized in that the drop and scatter ratio is controlled in a low range while using a larger hole than that of conventional techniques. Thus, a water absorbent resin having maintained or improved physical properties without having any coloration, uneven drying, or lowered yield can be obtained even when polymerization is carried out using an aqueous solution of a monomer with relatively high concentration.

(f) Drop and Scatter Ratio

The drop and scatter ratio described in the invention may be obtained by measuring the weight of a dried product which is dried without being dropped or scattered from a through-circulation belt or a through-circulation plate during the drying step. The drop and scatter ratio is represented by following Formula 1 when a through-circulation belt type dryer is used, or by following Formula 2 when a through-circulation stationary batch type dryer is used.

[Expression 5]

Drop and scatter ratio[% by weight]={1−(Amount of solid content in particulate hydrogel obtained from drying step/Amount of solid content in particulate hydrogel provided to through-circulation belt)}×100     [Formula 1]

[Expression 6]

Drop and scatter ratio[% by weight]={1−(Amount of solid content in particulate hydrogel obtained from drying step/Amount of solid content in particulate hydrogel provided to through-circulation plate)}×100     [Formula 2]

Alternatively, as a second method for measuring drop and scatter ratio, it may be also obtained by measuring a hydrogel that is scattered and lost (that is, in general, total amount of dropped and scattered hydrogel or dried product thereof) to the outside of a through-circulation belt between providing a particulate hydrogel to a through-circulation belt or a through-circulation plate and removing the gel from a dryer after the completion of drying. The drop and scatter ratio is represented by following Formula 5 when a through-circulation belt type dryer is used, or by following Formula 6 when a through-circulation stationary batch type dryer is used.

[Expression 7]

Drop and scatter ratio[% by weight]=(Amount of solid content in particulate hydrogel recovered from outside of through-circulation belt/Amount of solid content in particulate hydrogel provided to through-circulation belt)×100    [Formula 5]

[Expression 8]

Drop and scatter ratio[% by weight]=(Amount of solid content in particulate hydrogel recovered from outside of through-circulation plate/ Amount of solid content in particulate hydrogel provided to through-circulation plate)×100    [Formula 6]

Meanwhile, although the two measurement methods above are appropriately selected, the drop and scatter ratio is more conveniently and precisely determined by a method of measuring the weight of a dried product that is discharged without being dropped or scattered from a through-circulation belt or a through-circulation plate. In addition, since the drying on a through-circulation belt generally requires a large scale drying (amount and time), therefore, a test may be carried out by using a batch type stationary air circulation dryer as a model system, as described in the Example 1 below.

According to the invention, the drop and scatter ratio of a particulate hydrogel is 0 to 1% by weight, preferably 0 to 0.6% by weight, more preferably 0 to 0.5% by weight, still more preferably 0 to 0.4% by weight, particularly preferably 0 to 0.1% by weight, and most preferably 0 to 0.02% by weight. From the view point of yield, the lower limit is preferably 0% by weight. 0% by weight can be achieved by reducing a mesh size or hole of a through-circulation belt or a through-circulation plate. However, it may lower physical properties (water absorption capacity or extaractables). Therefore, it is sufficient that the lower limit is 0.001% by weight, or further 0.005% by weight. If it is not within the above range, physical properties related to absorption may be impaired (for example, GEX value explained below is lowered), coloration is caused, or drying efficiency or yield may be lowered. Since dropped residual materials that are accumulated at the bottom of the dryer may easily cause incorporation of black foreign materials under drying by heating for a long period of time, it is preferable that the dropped residual materials in the dryer (for example, dropped residual materials and others at the bottom of the dryer) are periodically removed from the dryer, for example within 180 days, 90 days, 1 month (30 days), or further 1 week in continuous drying. The removal can be manually carried out or mechanically or automatically carried out by using vacuum or a brush.

Further, although the dropped residual materials described above remain at the bottom and others of the dryer (for example, a band dryer shown in FIG. 3.6 of Non-Patent Literature 1) either temporarily or long term, they can be removed after stopping the drying or during running the drying.

A greater amount of the dropped residual materials are found in accordance with order of the solid content concentration in a particulate hydrogel, that is, 45% by weight or more, further 50% by weight or more, in the following order, 55% by weight or more, and 60% by weight or more, in particular. Meanwhile, although the upper limit of the solid content concentration in a particulate hydrogel is not specifically limited as long as it remains as a hydrogel, it is 80% by weight or less, further 75% by weight or less, and particularly 70% by weight or less. When the solid content concentration is less than 45% by weight, the effect expected from removing dropped residual materials may be difficult to obtain.

Specifically, the invention (third invention) relates to a method for producing a water absorbent resin including a polymerization step for polymerizing an unsaturated monomer and a drying step for drying a particulate hydrogel crosslinked polymer having a solid content concentration of 45% by weight or more which is obtained by micronizing the hydrogel crosslinked polymer during or after the polymerization. Also provided by the invention is a production method of using a through-circulation belt type dryer for drying in the drying step and removing periodically the dropped residual materials from a dryer.

The amount of the dropped residual materials to be removed is suitably determined depending on an amount of dropped and scattered materials, and it is removed as much as the entire amount (100% by weight) of the dropped and scattered materials. Since part of dropped and scattered materials is eliminated with hot air to the outside of a dryer, the entire amount of the dropped and scattered materials is not necessarily remained or adhered in the dryer. However, the removal is preferably carried out such that preferably 50 to 100% by weight, and particularly preferably 90 to 100% by weight of the residual materials remaining in a dryer, including those adhered onto the dryer belt, are periodically removed. In other words, the dropped and scattered materials remained in the dryer (excluding dried materials that are eliminated with hot air to the outside of the dryer) are removed and the removed amount is, within the range of not more than the amount of dropped and scattered materials, preferably 1% by weight or less, more preferably 0 to 0.6% by weight, still more preferably 0 to 0.5% by weight, further still more preferably 0 to 0.4% by weight, particularly preferably 0 to 0.1% by weight, and most preferably 0 to 0.02% by weight relative to entire dried products. By having the removal amount of dropped residual materials within the range described above, the drying efficiency is improved and coloration or deterioration of physical properties caused by incorporation of the dropped and scattered materials is prevented. According to the method described above, the drop and scatter ratio is controlled at the above-defined level, and therefore within such range the dropped and scattered materials are favorably removed from a dryer.

Meanwhile, exhibition of high drop and scatter ratio like more than 1% by weight of a hydrogel or bad influence of such drop and scatter ratio on physical properties is the characteristics of a hydrogel with high solid content concentration (solid content concentration of 45% by weight or more, or 50% by weight or more), and a conventional hydrogel having low solid content concentration (solid content concentration of 20 to 40% by weight) is free of such problem as having high adhesiveness. However, in order to solve the problems associated with deterioration of physical properties in high concentration polymerization, studies are made in the present invention, and as a result, it was surprisingly found that a tiny difference (in terms of numerical value) in drop and scatter ratio of a hydrogel during drying is related to the physical properties (see, FIG. 1), and therefore the deterioration problem of physical properties in high concentration polymerization is solved according to the control of drop and scatter ratio.

Meanwhile, for any case in which any one of a through-circulation belt type dryer and a through-circulation stationary batch type dryer is used as a dryer, the effect of the invention can be similarly achieved as long as the drop and scatter ratio is within the range described above. In other words, even when any one of a through-circulation belt type dryer and a through-circulation stationary batch type dryer is used, deterioration of physical properties related to absorption (for example, GEX value explained below is lowered), coloration, or lowered drying efficiency or yield may be prevented more by further lowering the drop and scatter ratio.

The drop and scatter ratio (sum of drop ratio and scatter ratio) may be measured every time finishing the drying step when a through-circulation stationary batch type dryer is used, or it may be measured after performing the drying step for several times. Further, when a through-circulation belt type dryer is used, it may be continuously measured at each specific time, or may be obtained as a total production amount (total solid content amount) from the total drop amount at pre-determined time or pre-determined day (example; calculated from total drop amount during one month and total production amount during one month, total drop amount corresponds to the weight of a water absorbent resin dropped from a through-circulation belt).

Loss to the outside of a through-circulation belt or loss to the outside of a through-circulation plate is caused by drop of a hydrogel particle from holes of a through-circulation belt or a through-circulation plate or by scatter of a hydrogel particle with hot air, or the like. In case of a continuous drying using a through-circulation belt type dryer, the drop ratio can be calculated by recovering the lost hydrogel after operation for a certain period of time, measuring a solid content amount, and obtaining the average value thereof. When the recovery may not be easily made, the drop ratio may be calculated by measuring the solid content amount in a hydrogel which is transferred from the drying step to the next step. Further, the solid content amount of a hydrogel that is provided to a through-circulation belt or a through-circulation plate remains constant as long as it is under the pre-determined polymerization condition.

The amount of dropped particulate hydrogel is reduced by decreasing the void size of a punching metal or a sieve hole size of a wire mesh, in particular, when they are smaller than the particle of a hydrogel. However, when the hole is small, there is a tendency that hot air is poorly circulated and thus the hydrogel or a dried product thereof is scattered. For such reasons, the drop and scatter ratio (sum of drop ratio and scatter ratio) is not simply determined by the hole size of a punching metal or a wire mesh. Instead, it is preferably controlled as described below (aggregation treatment of a hydrogel, in particular).

(g) Method for Controlling Drop and Scatter Ratio

As for the specific method for controlling drop ratio of a hydrogel, it is not specifically limited if the drop and scatter ratio is controlled in the above range by using a method exemplified in the section (2-3) above (moving speed of a belt, thickness of a hydrogel, area occupancy rate, and hole area ratio when a through-circulation belt type dryer is used), or the like. However, a method exemplified in the above (2-3) or others, in particular a means for aggregating particulate hydrogel, which is accumulated on a through-circulation belt or a through-circulation plate, at an early phase of drying, in other words, having an aggregation zone, that is, so called an aggregation treatment, is important. In this regard, one preferred embodiment of the invention is characterized in that an aggregation zone for aggregating particulate hydrogel is included on a through-circulation belt or a through-circulation plate in the drying step.

Examples of the method for aggregating the particulate hydrogel during the aggregation zone include the following (1) to (5). After undergoing at least one aggregation zone given below, the aggregated particulate hydrogel is dried at 150 to 250° C.;

(1) Ensuring aggregation time by suppressing drying speed at early phase of drying;

(2) Promoting aggregation by increasing hygroscopic moisture within a drying chamber at early phase of drying;

(3) Performing forced aggregation at early phase of drying by using a compression device;

(4) Performing forced aggregation at early phase of drying by spraying an aggregating agent; and (5) Aggregating particulate hydrogel by cooling it.

With regard to the specific condition for (1) above, since an aggregation property, that is, adhesive property among gel particles, is dramatically reduced when solid content concentration of a particulate hydrogel is more than 80% by weight, it is preferable that the hydrogel with high solid content concentration is aggregated to each other by having 5 minutes or more, or preferably 10 minutes or more of drying time in which the increase amount of the solid content concentration is the same or less than 10% by weight (or the same or less than 5% by weight, or substantially 0% by weight) and/or solid content concentration is the same or less than 80% by weight, or preferably the same or less than 75% by weight. The upper limit is appropriately determined by an aggregation property or the like. However, from the viewpoint of productivity or physical properties, it is 2 hr or less, 1 hr or less, or 0.5 hr or less, preferred in this order. There is a tendency that the productivity or physical properties are impaired by excessive aggregation treatment. Examples of a method for suppressing drying speed include windless or mild wind condition (for example, less than 2.0 [m/sec]) at room temperature to 150° C., further 80 to 150° C., and preferably 80° C. to 120° C. on a through-circulation belt or a through-circulation plate.

Meanwhile, the expression "early phase of drying" in the method (1) described above means from the start point of drying to the time point at which the increase amount of the solid content concentration is the same or less than 10% by weight and/or solid content concentration is the same or less than 80% by weight (ditto for the following methods (2) to (4)).

When a through-circulation belt type dryer has a multi-chamber structure, the period from the start point of drying of the particulate hydrogel to the time point at which the increase amount of the solid content concentration is maintained within the level of 10% by weight is preferably 5 min or more. Further, since a hydrogel with small size may easily be the reason for drop and scatter, weight average particle diameter (D50) of the particulate hydrogel is preferably 1 mm or more and more preferably 1.5 mm or more. By having the lower limit of the weight average particle diameter (D50) to be within the range above, rapid drying at early phase of drying can be prevented and an increase in solid content concentration can be suppressed.

Specific conditions for the above (2) include that the dew point inside the dryer (for a through-circulation belt type dryer having a multi chamber structure, inside of a drying chamber) is 70° C. to 100° C., and preferably 80° C. to 100° C. Temperature of the hot air is 80 to 150° C., and preferably 80° C. to 120° C. Further, the direction of hot air may be either up-flow, down-flow, or parallel to the surface of a through-circulation belt or a through-circulation plate. Further, it may be a combination thereof. When a through-circulation belt type dryer is used, in particular, it is preferable that the first part of the drying step is run in up-flow direction while the latter part is run in down-flow direction to easily achieve particulate hydrogel in even state. Time for such operation is from 1 min to 1 hour, or 5 min to 0.5 hour. After that, drying is favorably carried out at the temperature described above or more and the dew point or less.

As a specific condition for the above (3), the laminar of particulate hydrogel on a through-circulation belt or a through-circulation plate is compressed using a compression roll (press roll) and others before drying to improve bulk density of the hydrogel. It may be preferably compressed (bulk density is improved) by 1.01 to 5 times, further 1.05 to 3 times, or 1.1 to 2 times.

As a specific condition for the above (4), adding various binders to hydrogel before drying, in particular, spraying water, inorganic acid, or an organic acid-water solution of a low molecular weight or high molecular weight polymer may be exemplified. Since hydrogel of a water absorbent resin generally has higher adhesive property at low solid content concentration (particularly, 40% by weight or less, or 30% by weight or less) or low-neutralization (particularly in polyacrylic acid, neutralization rate of 0 to 50% by mole, preferably 0 to 30% by mole, more preferably 0 to 10% by mole, and still more preferably 0% by mole), only the surface of hydrogel is preferably adjusted to have low-neutralization rate or high water content. Examples of the organic acid or inorganic acid that are used include hydrochloric acid, sulfuric acid, acetic acid, propionic acid, sulfurous acid, polyacrylic acid, phosphoric acid, lactic acid, citric acid, and tartaric acid, or the like. By adding the acid in an amount of 0.001 to 10 parts by weight, or further 0.01 to 1 parts by weight relative to the solid content, the adhesive property on a surface of hydrogel is preferably improved. In general, the organic acid or inorganic acid has no contribution to water absorption. As such, when the using amount of the organic acid or inorganic acid is more than 10 parts by weight, it may be disadvantageous in terms of cost or water absorbing property (water absorption capacity per unit weight, CRC or AAP).

As a specific condition for the above (5), since the adhesive property of a hydrogel is increased at low temperature, after polymerization, the hydrogel is preferably cooled to a predetermined temperature, preferably 60° C. or less, in the following order, 50° C. or less, 40° C. or less, particularly 30° C. or less. Excessive cooling is disadvantageous in terms of energy required for drying, and therefore it is sufficient that the lower limit is room temperature.

Among the aggregation methods described above, only the methods of (1) to (5) may be carried out or only the method exemplified in the above (2-3) (regarding moving speed of a belt, thickness of hydrogel, area occupancy ratio, and hole area ratio) may be carried out. However, it is preferable that at least one method of (1) to (5) is carried out, and any one of (1) and (2) is preferably carried out. Further, the methods of (1) to (5) and the method exemplified in the above (2-3) may be carried out either singly or in combination of two or more.

Examples of an aggregation method other than the above (1) to (5) include the followings:

a method of providing (spraying) hydrogel on a through-circulation belt or a through-circulation plate such that thickness of the hydrogel is 5 cm or more;

a method of drying a hydrogel with gas having dew point of 50° C. or less after contacting it with gas having dew point of 50 to 100° C. for 5 min or more during drying step; and a method in which a through-circulation belt or a through-circulation plate is a punching metal, in particular the hole area ratio of a through-circulation belt or a through-circulation plate is from 20 to 50%.

Preferred aggregation method is the above (1) to (5), and also the above (1) and/or (2). The preferred drop and scatter ratio is in the following in order, 1% by weight or less, 0.6% by weight or less, 0.5% by weight or less, 0.4% by weight or less, 0.1% by weight or less, 0.05% by weight or less, and 0.02% by weight or less.

(h) Drying Temperature and Wind Speed after Aggregation Zone (Also Referred to as "Aggregation Treatment")

In the drying temperature range of 150 to 230° C., wind speed in a hot air dryer is controlled to 3.0 [m/sec] or less. In addition, the direction of hot air supplied to a through-circulation belt or a through-circulation plate may be either up-flow, down-flow, or parallel, or a combination thereof (for example, up-flow and down-flow in alternate motion). Among them, down-flow is preferable. When a through-circulation belt type dryer is used, in particular, it is preferable that the first part is run in up-flow direction while the latter part is run in down-flow direction to easily achieve even drying. Meanwhile, the hot air of up-flow or down flow is not limited to vertical direction (90°), and it may be also in tilted direction (around 90°, for example ±30° or so).

The drying temperature (defined by temperature of a heating medium, in particular, temperature of hot air) is preferably 150 to 230° C., more preferably 160 to 200° C., and still more preferably 170 to 190° C.

By drying the particulate hydrogel at the drying temperature of 150 to 230° C., the time required for drying can be shortened at the same time reducing coloration of a dried product obtained. As used herein, the drying temperature is defined by the temperature of a heating medium used when direct heating based on thermal conduction is performed by using oil or vapor as a heating medium (for example, a drum dryer or the like). When a material is indirectly heated with mediation of an air or the like having oil or vapor as a heating medium (for example, a through-circulation band dryer or the like), it is defined as the atmospheric temperature. Meanwhile, when drying is carried out without using a heating medium, irradiation with electronic beam or the like, it is defined as the temperature of the material (hydrogel polymer under drying).

(i) Drying Time after Aggregation Zone (Also Referred to as "Aggregation Treatment")

The drying time after aggregation zone varies depending on surface area of particulate hydrogel, water content ratio, and type of a dryer, and it is suitably selected so as to obtain desired water content ratio. For example, it is 10 to 120 min, and more preferably 20 to 60 min. A dried product obtained by drying a hydrogel crosslinked polymer during the drying step is pulverized and subjected to sizing treatment thereafter.

(j) Dew Point after Aggregation Zone

The dew point is preferably lowered after increasing it during the aggregation zone. It is preferable that the gas to be contacted with hydrogel polymer after the aggregation zone has dew point of less than 70° C., preferably 0 to less than 70° C., and particularly 20 to 60° C. By controlling it within this range, drying speed can be improved. Further, from the view point of residual monomers, water absorbing property, or coloration during the drying step, hot air with dew point which is higher at the entrance of a dryer than at the exit of a dryer, that is, preferably higher by 10 to 50° C., or further higher by 15 to 40° C. is preferably contacted with hydrogel. By controlling the dew point within this range, decrease in bulk density of dried powder can be also prevented.

Meanwhile, during the drying step of the invention, the particulate hydrogel is preferably contacted with steam-air mixture gas and/or steam-inert gas or steam.

(k) Means for Controlling Thickness and Area Occupancy Ratio of Hydrogel

As a specific means for controlling thickness of hydrogel (particulate hydrogel) at the time of using a through-circulation belt type dryer, it is not specifically limited if it can be controlled within the range described above. Examples thereof include the following (1) to (4) or the like, and they may be used in combination.

(1) Gel feed amount to a through-circulation belt type dryer is controlled in width direction.

(2) Thickness of a gel fed on a through-circulation belt is controlled by changing in width direction by using a control plate or roller or the like having a constant shape (for example, wave shape, comb-teeth shape, and saw-teeth shape).

(3) Thickness of a gel is controlled by supplying hydrogel to a through-circulation belt from several points in width direction and by making the hydrogel be ridged shape or the like on through-circulation belt. The thickness may be also controlled by modifying the feed amount of hydrogel at each supply point.

(4) Thickness of a gel is controlled by supplying hydrogel in many steps on a through-circulation belt so that the thickness of the hydrogel is modified.

In the above (1) to (4), as for the method of supplying hydrogel on a through-circulation belt, it may be directly fed to a through-circulation belt from en exit of an apparatus for polymerization step or micronization step (for example, kneader, meat chopper), or a feeder disclosed in Patent Literatures 3 and 18 to 20 or the like may be also used.

Specific examples of the control method include a method of using a traverse feeder or an oscillating feeder as an apparatus for supplying particulate hydrogel, and controlling sequentially a servo motor and an inverter motor of the apparatus. Further, when the particulate hydrogel is fed from the supplying apparatus to a through-circulation belt, gap between the supplying apparatus and a through-circulation belt is 20 to 80 cm, and in particular 30 to 50 cm. It is also preferable that it is fed from the supplying apparatus to a through-circulation belt based on free fall. By controlling a traverse feeder or an oscillating feeder, preferably by digitally controlling them (continuous on and off, or periodic speed change), the laminar of particulate hydrogel can be controlled within the range defined in (c) and (d) above. Meanwhile, control of an oscillating feeder is not disclosed in Patent Literatures 1 to 3.

(I) Materials or the Like of Through-Circulation Belt or Through-Circulation Plate The through-circulation belt or through-circulation plate installed in a through-circulation dryer may be one or more. It may be also formed as a multi-step drying apparatus based on their combination in series or parallel. For a through-circulation belt type dryer, it is preferable that only one through-circulation belt is installed in the dryer. Surface of the through-circulation belt or through-circulation plate may be previously treated like electric grinding or Teflon (registered trademark) treatment. Among them, the through-circulation belt or through-circulation plate is preferably a punching metal. Further, the punching metal is preferably made of stainless. Still further, thickness of the punching metal is preferably 0.3 to 10 mm, and more preferably 1 to 5 mm.

Surface roughness of a through-circulation belt or a through-circulation plate is preferably controlled so that the surface roughness is equal to or smaller than 800 nm, in terms of surface roughness (Rz) specified by JIS B 0601-2001. The surface roughness (Rz) may be smoothened to preferably equal to or smaller than 500 nm, more preferably equal to or smaller than 300 nm, still more preferably equal to or smaller than 200 nm, particularly preferably equal to or smaller than 185 nm, and most preferably equal to or smaller than 170 nm. Herein, the surface roughness (Rz) means the maximal value of the maximal height (μm) of the surface irregularity. The lower limit of the surface roughness (Rz) is 0 nm, but, about 10 nm and still more about 20 nm is sufficient, because there is no significant difference even in about 10 nm. Other surface roughness (Ra) is also specified by JIS B 0601-2001 and preferable value thereof is set the same as in surface roughness (Rz). Ra is more preferably equal to or smaller than 250 nm, and particularly preferably equal to or smaller than 200 nm. Surface roughness (Ra) can be measured with a probe-type surface roughness meter in accordance with JIS B 0651-2001.

(m) Bulk Density of Particulate Hydrogel

According to the invention, the bulk density of particulate hydrogel that is accumulated on a through-circulation belt or a through-circulation plate (laminar of particulate hydrogel), that is, density of non-dried laminar of particulate hydrogel, is less than 0.7 [g/cm$^3$], particularly less than 0.6 [g/cm$^3$], and preferably less than 0.55 [g/cm$^3$]. It is also preferably controlled to have lower limit of 0.35 [g/cm$^3$] or more. Examples of a method for controlling bulk density include dropping hydrogel at pre-determined height, or a spraying on a through-circulation belt at pre-determined speed when a through-circulation belt type dryer is used. For such case, when the gel after spraying is flattened on a roller or the like as described in Patent Literature 18 above, it is difficult to control the density.

Meanwhile, when a through-circulation belt type dryer is used, the bulk density of a laminar of particulate hydrogel can be calculated by measuring the weight of particulate hydrogel accumulated on the through-circulation belt from the inlet of a dryer till 1 min in moving direction and the volume of a laminar of a particulate hydrogel measured by using a laser type trip meter or scanning of a laser type displacement sensor.

(n) Dried Solid Content

According to the invention, it is preferable that the polymerization step and the gel micronization step are directly connected to each other so as to the hydrogel is directly provided to a drying step without being kept or stored. Further, regarding the drying step after aggregation zone, drying preferably by heating according to the following preferably (A) or (B), or more preferably by (A) and (B) is carried out.

(A) Once the aggregation zone is finished, preferably within 10 minutes, the particulate hydrogel is dried by heating until obtaining solid content concentration of 80% by weight or more. More preferably, it is dried to 85% by weight or more. Particularly preferably, it is dried to 90% by weight or more. The upper limit is not limited to 100% by weight (moisture content of 0% by weight). Rather, 99 to 94% by weight or so is sufficient.

(B) Once the aggregation zone is finished, within 10 minutes, solid content concentration of the particulate hydrogel crosslinked polymer is increased by 10% or more, further 20% or more, and particularly 30% or more. Further, within 5 minutes after the aggregation zone is finished, it is dried by heating until the solid content concentration is 65% by weight or more, and further 70% by weight or more. Although a technique of storing or performing a certain treatment of a hydrogel after polymerization but before drying is disclosed Patent Literature 17 or Patent Literature 19. However, the Patent Literatures don't disclose (A) or (B) described above, because the drying method of Patent Literature 17, Patent Literature 19 and others includes a certain time period (for example, 5 min or more) after the completion of polymerization, and therefore, it is substantially difficult to control the solid content concentration within the range described above.

For the control of (A) and (B), the polymerized gel taken from a polymerization reactor is continuously added to a dryer, and a retention time in the dryer is 1 min or less, preferably 0.5 min or less, and further 0.2 min or less. Further, the upper limit of the solid content concentration between the start of drying after finish of the aggregation zone and the completion of drying step for 5 min to 10 min is 90% by weight or less, and further 85% by weight or less. Further, temperature of a hydrogel crosslinked polymer added to a dryer is controlled to preferably 50 to 80° C., and still more preferably 60 to 70° C.

(o) Additives for Drying Step

During the drying step of the invention, additives or the like that are described in the above (10) or Patent Literatures 21 to 26 may be added for promoting aggregation of hydrogel or depending on other purposes. Preferably, water absorbent resin fine powder is added to hydrogel before drying in an amount of further 1 to 40% by weight, particularly 10 to 30% by weight (relative to solid content).

In addition to above, if necessary, a vaporized monomer recycling step, an agglomerating step, a fine powder removing step, a fine powder recycling step and/or like steps may be further included. Further, the following additives can be added to the monomer or a polymer thereof so as to attain a stability of a color hue that changes over time, prevention of deterioration in gel, or the like.

According to the invention, it is preferable that a step for recycling the water absorbent resin fine powder obtained after the size classification step is further included before the drying step. Specifically, a step for recycling the water absorbent resin fine powder or hydrated adduct thereof to the polymerization step or the drying step is included. By recycling of fine powder, particle size control, water absorbing speed, or a liquid permeability can be improved. The recycling amount of fine powder is suitably determined within the range of 0.1 to 40% by weight, further 1 to 30% by weight, and particularly 5 to 25% by weight in the pulverized product.

(2-4) Pulverizing Step and Size Classification Step

It is a step for pulverizing and sieving the dried product obtained from the drying step above to give a water absorbent resin.

According to this step, the dried product obtained from the above drying step may be used as it is as dry powder. However, it is preferable to adjust the particle size to a specific value in order to improve a physical property in surface crosslinking step described below. The adjustment of the particle size is not limited to the pulverizing step or size classification step, and it may be carried out in polymerization (particularly the reverse phase suspension polymerization), collection of fine powder, granulation, or the like. In the description discussed hereinafter, the particle size is defined by a standard sieve (JIS Z8801-1 (2000)).

The crusher which may be used for the pulverizing step is not specifically limited and any conventionally known crusher may be used. Specific examples thereof include roll mill, hammer mill, roll granulator, jaw crusher, gyratory crusher, cone crusher, roll crusher, and cutter mill, or the like. Of these, from the view point of size control, multi-level roll mill or roll granulator is preferably used.

For size classification step, various size classifying apparatuses based on sieve classification or air stream classification or the like may be used. When the surface crosslinking is performed as described below, the size classification step (the first size classification step) is preferably performed before the surface crosslinking step. More preferably, an additional size classification step is performed after the surface crosslinking step (the second size classification step).

From the view point of improving the physical properties of the water absorbent resin obtained from this step, it is preferable that the particle size is adjusted so as to make the particle size be as follows. Specifically, the weight average particle diameter (D50) of the water absorbent resin prior to the surface crosslinking is preferably 200 to 600 μm, more preferably 200 to 550 μm, still more preferably 250 to 500 μm, and particularly preferably 350 to 450 μm. It is preferable that the ratio of fine particles (particle size of less than 150 μm) which can pass through a sieve with sieve mesh size of 150 μm (JIS standard sieve) is preferably 0 to 5% by weight, more preferably 0 to 3% by weight, and still more preferably 0 to 1% by weight relative to the entire water absorbent resin. It is preferable that the ratio of large particles (particle size of more than 850 μm) which may not pass through a sieve with sieve mesh size of 850 μm (JIS standard sieve) is preferably 0 to 5% by weight, more preferably 0 to 3% by weight, and still more preferably 0 to 1% by weight relative to the entire water absorbent resin. A logarithmic standard deviation ($\sigma\zeta$) of particle size distribution of the water absorbent resin is preferably 0.20 to 0.40, more preferably 0.25 to 0.37, and still more preferably 0.25 to 0.35. The particle size may be defined by standard sieve classification, and it is measured by the method disclosed, in EDANA-ERT 420.2-02 (particle size distribution) with reference to the method of WO 2004/69915 (weight average particle diameter, $\sigma\zeta$).

Generally when the water absorbent resin is controlled to have narrow particle size distribution, that is, it is controlled to have a small difference between the upper limit and lower limit of the particle size, coloration of a water absorbent resin is significant when measuring color hue. However, no such problem in color hue is found in the invention, and therefore desirable. Thus, for the particle size distribution of the water absorbent resin obtained by the invention, the ratio having particle size of 150 to 850 μm is 95% by weight or more, and preferably 98% by weight or more (upper limit is 100% by weight).

(2-5) Surface Crosslinking Step

The crosslinked polymer (base polymer) obtained from the drying step above may have a crosslinked surface. In other words, a method for producing a water absorbent resin having a crosslinked surface after drying step of the invention is also included in the invention.

This step is a step of crosslinking (surface crosslinking reaction) near the surface of a water absorbent resin obtained from the above pulverizing step and size classification step with a surface crosslinking agent for improving water absorbing property, if necessary. According to the surface crosslinking treatment, it is possible to obtain a water absorbent resin having less coloration and higher whiteness. The step is particularly preferably applied for a water absorbent resin which employs surface crosslinking carried out at high temperature. In addition, when the water absorbent resin obtained by the invention is used as a raw material for a hygienic product (in particular, a disposable diaper), it is preferable to improve an absorption against pressure (AAP) of the water absorbent resin to 20 [g/g] or higher by the surface crosslinking treatment.

A method for surface crosslinking is not especially limited, and it includes, for example, a method for performing crosslinking polymerization by adding a monomer to the surface of a water absorbent resin, a method for performing radical crosslinking by adding a radical polymerization initiator, and a method for performing radiation crosslinking by heat or radiation (preferably, UV ray). Preferably, surface of the water absorbent resin is further crosslinked (secondary crosslinking) by adding a surface crosslinking agent which is capable of reacting with a functional group of the water absorbent resin.

Herein below, surface crosslinking method by using a surface crosslinking agent is described.

As the surface crosslinking agent, various organic crosslinking agents or inorganic crosslinking agents can be used in the invention without specific limitation. Among them, an organic surface crosslinking agent is preferable, and combined use of an organic surface crosslinking agent and an ionic crosslinking agent is more preferable. Specific examples thereof include polyhydric alcohol compound, epoxy compound, polyvalent amine compound, or a condensate between these compounds and halo-epoxy compound; oxazoline compound, (mono, di, or poly)oxazolidinone compound, and alkylene carbonate compound. In particular, dehydrated ester reactive crosslinking agent consisting of polyhydric alcohol compound, alkylene carbonate compound, and oxazolidinone compound which requires reaction at high temperature may be used. More specific examples thereof include the compounds exemplified in U.S. Pat. Nos. 6,228,930, 6,071,976, 6,254,990 and the like. For example, there are included polyhydric alcohol compound such as mono, di, tri, tetra-propylene glycol, 1,3-propanediol, glycerin, 1,4-butanediol, 1,3-butanediol, 1,5-pentanediol, 1,6-hexanediol, and sorbitol; epoxy compound such as ethylene glycol diglycidyl ether and glycidol; alkylene carbonate compound such as ethylene carbonate; oxetane compound; and cyclic urea compound such as 2-imidazolidinone, or the like. Using amount of the surface crosslinking agent described above is appropriately determined to be in the range of preferably 0.001 to 10 parts by weight, and more preferably 0.01 to 5 parts by weight, relative to 100 parts by weight of the water absorbent resin.

In addition, in the mixing of a water absorbent resin and a surface crosslinking agent, use of water as a solvent is preferable. Using amount of water in this case is appropriately determined in the range of preferably 0.5 to 20 parts by weight, and more preferably 0.5 to 10 parts by weight, relative to 100 parts by weight of the water absorbent resin. Further, in addition to water, a hydrophilic organic solvent may be used in combination, if necessary. The using amount thereof is appropriately determined in the range of preferably 0 to 10 parts by weight, and more preferably 0 to 5 parts by weight, relative to 100 parts by weight of the water absorbent resin. Further, within the range of the effect of the invention, water insoluble fine particle powder or a surfactant may be also present at the time of mixing with a surface crosslinking solution. The type and using amount or the like of the fine particle powder or a surfactant is exemplified in U.S. Pat. No. 7,473,739 and the like, and the using amount thereof is appropriately determined in the range of preferably 0 to 10 parts by weight, more preferably 0 to 5 parts by weight, and still more preferably 0 to 1 part by weight relative to 100 parts by weight of the water absorbent resin.

According to the present step, it is preferable that the water absorbent resin be subjected to heat treatment after mixing with the surface crosslinking agent. After that, it is subjected to cooling treatment, if necessary. Heating temperature for performing the heat treatment described above is preferably from 70 to 300° C., more preferably 120 to 250° C., and still more preferably from 150 to 250° C. When the treatment temperature is less than 70° C., the heating treatment time may be extended, resulting in lowered productivity. There is also a problem that an even surface crosslinking layer may not be formed. On the other hand, when the treatment temperature described above is more than 300° C., the water absorbent resin may be deteriorated. The heating time for the heating treatment is preferably in the range of 1 min to 2 hours. The heating treatment may be carried out by using a common dryer or heating furnace.

It should be noted that, the surface crosslinking methods that are described in EP Patent Nos. 0 349 240, 0 605 150, 0 450 923, 0 812 873, 0 450 924, 0 668 080, JP-A Nos. 7-242709, 7-224204, U.S. Pat. Nos. 5,409,771, 5,597,873, 5,385,983, 5,610,220, 5,633,316, 5,672,633, 5,462,972, WO 99/42494, 99/43720, or 99/42496, or the like may be also preferably applied to the invention.

(2-6) Fine Powder Recycling Step

This step is a step for recycling fine powder (in particular, fine powder containing powder with particle size of 150 μm or less in an amount of 70% by weight of more) separated from the drying step and, if necessary, the pulverizing step or size classification step, to the polymerization step or the drying step, either as it is or after hydrated, and a method disclosed in US Patent Application Publication No. 2006/247351 or U.S. Pat. No. 6,228,930 can be applied. By recycling of fine powder, particle size of the water absorbent resin can be controlled and high solid content concentration can be easily achieved by adding the fine powder. As the water absorbent resin after drying can be easily released from a through-circulation belt or a through-circulation plate (in particular, through-circulation belt) of a dryer, and therefore it is desirable.

(2-7) Other Steps

In addition to the steps described above, a surface treatment step using a polyvalent metal, a vaporized monomer recycling step, a granulating step, and a fine powder removing step may be included, if necessary. The above additives can be added as necessary, to any one or all of the steps described above so as to attain a stability of the color hue that changes over time, prevention of deterioration in gel, or the like.

The surface treatment step using polyvalent metal salt is applied when high liquid permeability against pressure (SFC or GBP) is required. The method disclosed in U.S. Pat. No. 6,605,673 or 6,620,889 is employed depending on necessity.

[3] Physical Properties of Water Absorbent Resin

The water absorbent resin of the invention contains polyacrylic acid (salt)-type water absorbent resin as a main component, and in case of using it in hygienic products, particularly a disposable diaper, it is obtained by the polymerization or the surface crosslinking or the like described above. Regarding the water absorbent resin obtained thereby, among the physical properties of the following (3-1) through (3-7), preferably at least one physical property is controlled, more preferably two or more physical properties including AAP are controlled, and particularly three or more physical properties are controlled. If the water absorbent resin does not satisfy each physical property described below, sufficient performance may not be obtained from high-concentration diaper containing a water absorbent resin at the concentration of 40% by weight or more.

(3-1) Initial Phase Color Hue

The water absorbent resin obtained by the invention is preferably white powder as it is used as a raw material for hygiene products like a disposable diaper. Thus, in a Hunter Lab color system measurement by spectrophotometric colorimeter, the water absorbent resin has a value "L" (lightness), as initial phase color hue, preferably 85 or more, more preferably 87 or more, and still more preferably 89 or more. And, value "a" is preferably −2 to 2, more preferably −1 to 1, still more preferably −0.5 to 1, and particularly preferably 0 to 1. value "b" is preferably −5 to 10, more preferably −5 to 9, still more preferably −4 to 8, and particularly preferably −1 to 7.

Although the upper limit of the value "L" is 100, when it is 85 or more, a problem related with color hue does not occur in hygiene products or the like. Also, the water absorbent resin of the invention has a YI (Yellow Index) value of preferably not more than 10, more preferably not more than 8, and still more preferably not more than 6, and WB (white balance) value of preferably 70 or more, more preferably 75 or more, and still more preferably 77 or more.

The initial phase color hue indicates the color hue of a water absorbent resin after production, and it generally represents the color hue measured before factory shipment. However, if stored under condition including temperature of 30° C. or less and relative humidity of 50% RH, a color hue measured within a year from the production can be adopted as the color hue.

(3-2) CRC (Water Absorption Capacity without Load)

A CRC (Water absorption capacity without load) of the water absorbent resin obtained by the invention is preferably 10 [g/g] or more, more preferably 20 [g/g] or more, still more preferably 25 [g/g] or more, and particularly preferably 30 [g/g] or more. The upper limit of CRC is, although not specifically limited, preferably 50 [g/g] or less, more preferably 45 [g/g] or less, and still more preferably 40 [g/g] or less. When the CRC is less than 10 [g/g], an absorption amount of a water absorbent resin is low, and therefore it may not be appropriate to use it as an absorber in hygiene products like a disposable diaper. On the other hand, when the CRC is higher than 50 [g/g], hygiene products having good liquid-absorption speed may not be obtained when the water absorbent resin is used as an absorber. CRC can be appropriately controlled by using the internal crosslinking agent or the surface crosslinking agent described above.

(3-3) AAP (Absorption Against Pressure)

In order to prevent a leakage from a disposable diaper, AAP (absorption against pressure) of the water absorbent resin obtained by the invention is preferably 20 [g/g] or more, more preferably 22 [g/g] or more, and still more preferably 24 [g/g] or more against pressure of 1.9 kPa or still more preferably 4.8 kPa, in which the drying is a means to achieve it. In consideration of a balance between AAP and other physical properties, the upper limit of AAP is set at 40 [g/g] or less, although not specifically limited thereto. When AAP is less than 20 [g/g], and such water absorbent resin is used as an absorbent core, it may be impossible to obtain hygiene products in which return of the liquid once absorbed (in general, it is also referred to as "re-wet") by applying a pressure to the absorbent core is small. The AAP may be appropriately controlled by using the surface crosslinking agent or particle size or the like mentioned above.

(3-4) SFC (Saline Flow Conductivity)

In order to prevent leakage from a disposable diaper, SFC (saline flow conductivity) of the water absorbent resin obtained by the invention is, as liquid permeability SFC of a liquid against pressure, preferably 1 $[\times 10^{-7} \cdot cm^3 \cdot s \cdot g^{-1}]$ or more, more preferably 10 $[\times 10^{-7} \cdot cm^3 \cdot s \cdot g^{-1}]$ or more, still more preferably 50 $[\times 10^{-7} \cdot cm^3 \cdot s \cdot g^{-1}]$ or more, particularly preferably 70 $[\times 10^{-7} \cdot cm^3 \cdot s \cdot g^{-1}]$ or more, and most preferably 100 $[\times 10^{-7} \cdot cm^3 \cdot s \cdot g^{-1}]$ or more, and the drying is a means to achieve it. The upper limit of SFC is preferably 3000 $[\times 10^{-7} \cdot cm^3 \cdot s \cdot g^{-1}]$ or less, and more preferably 2000 $[\times 10^{-7} \cdot cm^3 \cdot s \cdot g^{-1}]$ or less, although not particularly limited thereto. When the SFC is higher than 3000 $[\times 10^{-7} \cdot cm^3 \cdot s \cdot g^{-1}]$ and such absorbent resin is used for a water absorbent core, liquid spill from the water absorbent core may occur. The SFC may be appropriately controlled by the drying method or the like mentioned above.

(3-5) Ext (Water Extractables)

Ext (water extractables) of the water absorbent resin obtained by the invention is preferably 35% by weight or less, more preferably 25% by weight or less, still more preferably 15% by weight or less, and particularly preferably 10% by weight or less. When the Ext is higher than 35% by weight, gel strength of the water absorbent resin obtained may be weak and liquid permeability may be lowered. When such absorbent resin is used for a water absorbent core, it may be impossible to obtain a water absorbent resin in which return of the liquid once absorbed (i.e., re-wet) by applying a pressure to the absorbent core is small. Ext may be appropriately controlled by using an internal crosslinking agent or the like mentioned above.

(3-6) Residual Monomers (Residual Monomers)

From the viewpoint of safety, an amount of the Residual Monomers (residual monomers) of the water absorbent resin obtained by the invention is controlled to preferably 0 to 400 ppm, more preferably 0 to 300 ppm, and still more preferably 0 to 200 ppm. The residual monomers may be appropriately controlled according to the polymerization method or the like described above.

(3-7) GEX Value

GEX value of the water absorbent resin obtained by the invention is preferably 21 or more, more preferably 22 or more, and still more preferably 23 or more. Although CRC (Water absorption capacity without load) and Ext (water extractables) of the water absorbent resin contradict each other, the larger GEX value is more preferred as an indicator showing their relative relationship. However, the upper limit is 100 or so.

[4] Use of Water Absorbent Resin

Applications of the water absorbent resin that is obtained by the production method of the invention are not particularly limited, and preferably, it may be used in hygiene products such as a disposable diaper, a sanitary napkin, an incontinent pad, and absorbing articles such as a water retaining material for agricultural and horticultural use, an agent for solidifying waste liquid, or a water stopping agent for industrial use.

The water absorbent resin obtained by the invention exhibits particularly excellent performance when it is used in an absorbing article using water absorbent resin at high concentration. Content of the water absorbent resin in the absorber in these absorbing articles (core concentration) is preferably from 30 to 100% by weight, more preferably from 40 to 100% by weight, still more preferably from 50 to 100% by weight, further still more preferably from 60 to 100% by weight, particularly preferably from 70 to 100% by weight, and most preferably from 75 to 95% by weight. By containing the core concentration in the above-described amount, effect of the invention is exerted still more significantly, which is preferable. In the case where the water absorbent resin obtained by the invention is used in the range of the core concentration, in particular, at the upper layer of the absorbent core, the core exhibits superior capability of spreading of liquid such as urine due to the high liquid permeability (liquid permeability against pressure), and, absorbing amount of the absorbing articles, such as disposable diaper, in total is enhanced due to the efficient liquid distribution, therefore that is preferable. Further, it is also preferable that the invention provides absorbing articles which can maintain white color showing cleanliness.

In addition, it is preferable that the above absorber is compression molded so as to have a density of from 0.06 to 0.50 [g/cm$^3$], and a basis weight of from 0.01 to 0.20 [g/cm$^2$]. Further, thickness of the above absorber is preferably 30 mm or less, more preferably 20 mm or less, and still more preferably 10 mm or less, and thus the absorbent articles suitable for a thin-type disposable diaper can be provided.

EXAMPLES

Herein below, the invention will be described in view of the Examples and the Comparative examples. However, the invention should not be construed to be limited by them. For the sake of convenience, "liter" may be described as "L" and "% by weight" may be described as "wt %". Meanwhile, various physical properties of the water absorbent resin obtained by the invention, that are described in the claims or the examples, are obtained by the following measurement method under the condition including room temperature (20 to 25° C.) and humidity of 50 RH %, unless specifically described otherwise.

[1] Initial Phase Color Hue and Color Hue Over Time

Color hue of the water absorbent resin obtained by the invention was measured by the measurement method disclosed in WO 2009/005114. In particular, the color hue measurement of the water absorbent resin was assessed according to Hunter Lab color measuring system. Meanwhile, as a measurement device (spectrophotometric colorimeter), Lab Scan (registered trademark) XE manufactured by Hunter Lab was used. With regard to a measurement condition, reflection measurement was selected. A powder/paste sample container (an internal diameter of 30 mm and a height of 12 mm), a powder/paste standard round white board No. 2, and a 30Φ light projection pipe were also used.

The powder/paste sample container was charged with about 5 g of the water absorbent resin. The value "L" (Lightness: lightness index), value "a", and value "b" of the water absorbent resin surface were measured with the spectrophotometric colorimeter under atmosphere at room temperature (20 to 25° C.) and 50 RH % of relative humidity.

According to the invention, color hue of the water absorbent resin which is stored within a year from the production under atmosphere at temperature of 30° C. or less and relative humidity of 50 RH % or less, or which is right after produced, is referred to as "initial phase color hue", and the value "L" measured at that time was designated as "lightness index before exposure".

Further, as a "coloration acceleration test", the following operation was performed and the "lightness index after exposure" was measured.

The coloration acceleration test was carried out by putting a powder and paste sample container filled with about 5 g of the water absorbent resin into an incubator (compact environment tester series SH-641, manufactured by ESPEC Corporation), which had been adjusted to the temperature of 70±1° C. and relative humidity of 65±1 RH %, and keeping the container to be exposed to the atmosphere for 7 days.

Color hue of the water absorbent resin after the exposure is defined as "color hue over time" and the value "L" measured at the time is defined as "lightness index after exposure".

Meanwhile, whiteness level increases as the value "L" is closer to 100. As the value "a" and value "b" are closer to 0 (zero), it indicates less coloration, and therefore substantially white color.

By using the measurement device described above, other colors (YI; yellow Index (yellowness), and WB; white balance) can also be measured simultaneously. The smaller the value of YI is and the greater the value of WB is, the less the coloration is. That means the color is closer to substantially white.

[2] Solid Content Concentration

In an aluminum cup with bottom surface diameter of about 50 mm, 1.00 g of the water absorbent resin was weighed and total weight W1 [g] of a sample (including the water absorbent resin and aluminum cup) was precisely weighed.

Subsequently, the sample was placed in an oven at the atmospheric temperature of 180° C. to dry the water absorbent resin. Three hours later, the sample was taken out of the oven and then cooled to room temperature in a desiccator. After that, the total weight W2 [g] of a sample after drying (including the water absorbent resin and aluminum cup) was weighed and the solid content concentration (unit; [% by weight]) was calculated according to the following Formula 7.

[Expression 9]

$$\text{Solid content concentration[\% by weight]} = 100 - \{(W1-W2)/(\text{Weight of water absorbent resin[g]}) \times 100\} \quad \text{[Formula 7]}$$

Meanwhile, the measurement of solid content concentration in particulate hydrogel crosslinked polymer was carried out in the same manner as above except that the using amount of hydrogel was set to about 2 to 4 g and the drying time was set to 24 hours.

[3] SFC (Saline Flow Conductivity)

SFC (saline flow conductivity) of the water absorbent resin obtained according to the invention was measured by the method described in U.S. Pat. No. 5,669,894.

[4] GEX Value

A GEX value of the water absorbent resin obtained by the invention was calculated according to the description of US Patent Application Publication No. 2006/0167198. Letting y [g/g] be the value of CRC (water absorption capacity without load) and x [% by weight] be the amount of Ext (water extractables), the GEX value was defined by the Formulae 8 and 9 below.

[Expression 10]

$$GEX\,\text{value}(x>1)=(y+17)/ln(x) \quad \text{[Formula 8]}$$

[Expression 11]

$$GEX\,\text{value}(x\leq 1)=y/x \quad \text{[Formula 9]}$$

The GEX value is a parameter to evaluate the relation between two contradictory physical properties (CRC and Ext) of the water absorbent resin unambiguously, and the greater the GEX value, the better the performance of the water absorbent resin.

[5] Other Physical Properties

Physical properties such as a CRC (water absorption capacity without load), particle size distribution (see, the "PSD" section above: method disclosed in ERT 420.2-02), water extractables (see the "Ext" section above; method disclosed in ERT 470.2-02), and amount of residual acrylic acid (see the "Residual monomers" section above; method disclosed in ERT 410.2-02) of the water absorbent resin were measured in accordance with EDANA ERT or US Patent Application Publication No. 2006/204755.

Comparative Example 1

With reference to the Examples 3 of U.S. Pat. No. 6,906,159, acrylic acid salt having monomer concentration of 55% by weight and neutralization rate of 60% by mole was polymerized by UV ray. By crushing the gel with a vertical type crusher, a hydrogel crosslinked polymer was obtained.

Specifically, a mixture solution (A) containing 139.5 g of acrylic acid (monomer), 0.09 g of polyethylene glycol diacrylate (number average molecular weight of 478) (0.0097% by mole, relative to the monomer; internal crosslinking agent), and 0.02 g of 2-hydroxy-2-methyl-1-phenyl-propan-1-one (photodegradable polymerization initiator) and NaOH aqueous solution (B) in which 95.8 g of 48.5% by weight NaOH aqueous solution (basic material for neutralization) was diluted with 61.2 g of ion exchange water and added with 0.02 g of diethylenetriamine pentaacetic acid•pentasodium salt (chelating agent) were prepared separately and deaerated for 30 min under nitrogen gas atmosphere. The NaOH aqueous solution (B) was stirred using a magnetic stirrer and the solution (A) was added thereto all at once in an open system. After mixing, an aqueous solution of monomer was obtained. Although precipitates were observed at the initial stage of mixing, they were quickly dissolved and the liquid temperature was increased to about 90° C. by heat of neutralization and dissolution. The monomer concentration in the obtained aqueous solution of monomer was 55% by weight and the neutralization rate was 60% by mole.

Subsequently, 0.58 g of 10% by weight sodium persulfate aqueous solution (thermally degradable polymerization initiator) was added to the monomer solution described above. After stirring for several seconds, the mixture was immediately poured into a stainless tray container (surface temperature; about 64° C.) which had been placed on a hotplate heated to 90° C. (thickness of the solution; about 5 mm) in an open system. The stainless tray container had a size as follows: bottom surface 200×260 mm, top surface 560×460 mm, height 140 mm, trapezoidal at the central cross-section, and open at the top. A silicone sheet was adhered on an inner wall of the stainless tray container. Immediately thereafter, ultraviolet light was irradiated with a black light mercury lamp (peak wavelength of 352 nm, model No. H400BL, fitted within a projector MT-4020, both the lamp and the projector were products of TOSHIBA LIGHTING & TECHNOLOGY CORPORATION) to initiate polymerization. While the polymerization proceeded with generating water vapor, expanding in all directions and foaming, and then the polymerization system shrank to almost the same size as the original. The hydrogel crosslinked polymer crept up the tilt of the sides of the container when expanding, and then, the hydrogel crosslinked polymer stopped its movements at the state that it was larger than the size of the bottom of the container, when shrinking, but, it returned toward their original places. The resultant polymer expanded to about 30 times as large as the volume of the aqueous monomer solution at the maximum. The expansion and shrinkage ended within about 1 minute and, when the UV irradiation for 2 minutes had been completed, the hydrogel crosslinked polymer was taken out. From the record of the change in temperature of the polymerization system, the polymerization initiation temperature was 88° C. and the highest temperature was 111° C. The resultant hydrogel crosslinked polymer was in a much wrinkly because the bubbles either as is or collapsed, according to the size of bubbles.

The hydrogel crosslinked polymer obtained by the polymerization step described above was crushed at 50° C. with vertical type pulverizer (model No. VM27-S produced by Orient Co., Ltd., screen mesh opening size of 12 mm), thus, particulate hydrogel crosslinked polymer (1) with fluidity was obtained. The obtained particulate hydrogel crosslinked polymer (1) had a CRC of 33 [g/g], a water extractables of 6% by weight, a residual monomer content of 600 ppm, solid content concentration of 70% by weight, and weight average particle diameter (D50) of 2.5 mm.

Subsequently, 2 kg of the particulate hydrogel crosslinked polymer (1) obtained by plural polymerizations was placed on a through-circulation plate (material was SUS 304, hole was round and long holes and staggered, width of 1.2 mm, length of 15 mm; hole area ratio was 27%, size 15 cm×15 cm, surface roughness (Rz); 150 nm) made of a punching metal and dried to obtain comparative dried product (1). The drying was carried out by blowing hot air with temperature of 170° C. and dew point of 5° C. from the bottom to the top of the through-circulation plate for 20 min at blowing speed of 1.6 [m/sec]. The drop and scatter ratio from the through-circulation plate was 1.2% by weight.

After that, the comparative dried product (1) was pulverized with a roll mill and the obtained pulverized product was subjected to size classification by using JIS standard sieve with sieve mesh size of 600 μm and 300 μm. As a result, a comparative water absorbent resin (1) mostly having particle size of from 300 to 600 μm (weight average particle diameter (D50) of 460 μm) was obtained. Various physical properties including CRC of the obtained comparative water absorbent resin (1) are summarized in the Table 1.

Example 1

The particulate hydrogel crosslinked polymer (1) obtained in the Comparative example 1 was placed on a through-circulation plate and kept for 30 min in an atmosphere of 100° C. with dew point of 85° C. under no air stream condition to aggregate (aggregation treatment) a particulate hydrogel crosslinked polymer (1). And then, hot air with temperature of 170° C. and dew point of 5° C. was blown from the bottom to the top of the through-circulation plate for 20 min at blowing speed of 1.6 [m/sec]. Except for the operations above, the same operations as those of the Comparative example 1 were carried out to yield a dried product (1). The drop and scatter ratio from the through-circulation plate was 0.5% by weight.

After that, the dried product (1) was pulverized with a roll mill and the resulting pulverized product was subjected to size classification in the same manner as the Comparative example 1. As a result, a water absorbent resin (1) mostly having particle size of from 300 to 600 μm (weight average particle diameter (D50) of 450 μm) was obtained. Various physical properties of the obtained water absorbent resin (1) are summarized in the Table 1.

Example 2

The particulate hydrogel crosslinked polymer (1) obtained in the Comparative example 1 was placed on a through-circulation plate. Hot air with temperature of 140° C. and dew point of 75° C. was blown from the bottom to the top of the through-circulation plate for 10 min at blowing speed of 1.6 [m/sec] to aggregate (aggregation treatment) the particulate hydrogel crosslinked polymer (1). And then, hot air with temperature of 170° C. and dew point of 5° C. from the top to the bottom of the through-circulation plate for 20 min at blowing speed of 1.6 [m/sec]. Except for the operations above, the same operations as those of the Comparative example 1 were carried out to yield a dried product (2). The drop and scatter ratio from the through-circulation plate was 0.4% by weight.

After that, the dried product (2) was pulverized with a roll mill and the resulting pulverized product was subjected to size classification in the same manner as the Comparative example 1. As a result, a water absorbent resin (2) mostly having particle size of from 300 to 600 μm (weight average particle diameter (D50) of 460 μm) was obtained. Various physical properties of the obtained water absorbent resin (2) are summarized in the Table 1.

Example 3

The particulate hydrogel crosslinked polymer (1) obtained in the Comparative example 1 was placed on a through-circulation plate and compressed by 1.1 times or more from up above by using a compression roll to aggregate (aggregation treatment) the particulate hydrogel crosslinked polymer (1). And then, hot air with temperature of 170° C. and dew point of 5° C. from the bottom to the top of the through-circulation plate for 20 min at blowing speed of 1.6 [m/sec]. Except for the operations above, the same operations as those of the Comparative example 1 were carried out to yield a dried product (3). The drop and scatter ratio from the through-circulation plate was 0.4% by weight.

After that, the dried product (3) was pulverized with a roll mill and the resulting pulverized product was subjected to size classification in the same manner as the Comparative example 1. As a result, a water absorbent resin (3) mostly having particle size of from 300 to 600 μm (weight average particle diameter (D50) of 450 μm) was obtained. Various physical properties of the obtained water absorbent resin (3) are summarized in the Table 1.

Comparative Example 2

By line mixing, partial sodium salt solution of acrylic acid (monomer concentration of 53% by weight) with neutralization rate of 70% by mole containing 0.03% by mole (relative to monomer) of polyethylene glycol diacrylate (number average molecular weight of 478) as an internal crosslinking agent was continuously mixed with 0.04 g of sodium persulfate (relative to 1 mol of monomer; thermally degradable polymerization initiator) and 100 ppm of diethylenetriamine pentaacetic acid/pentasodium salt (chelating agent; the concentration relative to solid content). After that, the mixture was fed to a belt polymerization reactor to perform aqueous solution polymerization.

The hydrogel crosslinked polymer obtained by the aqueous solution polymerization step described above was crushed at 50° C. with vertical type pulverizer (model No. VM27-S produced by Orient Co., Ltd., screen mesh opening size of 12 mm), thus, particulate hydrogel crosslinked polymer (2) with fluidity, in which the solid content concentration was 70% by weight, was obtained. The obtained particulate hydrogel crosslinked polymer (2) had a CRC of 25 [g/g], a water extractables of 2.3% by weight, a residual monomer content of 600 ppm, and weight average particle diameter (D50) of 2.6 mm.

Subsequently, the obtained particulate hydrogel crosslinked polymer (2) was introduced to a through-circulation belt type dryer with an aid of a traverse feeder and dried to obtain a comparative dried product (2). For the drying, by sequence control of the traverse feeder, the particulate hydrogel crosslinked polymer (2) was continuously accumulated on a through-circulation belt (punching metal) which is working sequentially. The drying time was 35 min. Meanwhile, the dryer and other drying conditions are as described in the following (a) to (c).

(a) Through-Circulation Belt Type Dryer

As a through-circulation belt type dryer, a dryer having total six chambers which have the same volume and individually controllable temperature setting was used. The transit time for each drying chamber was about 5.8 min (35 min on through-circulation belt/6 chambers).

(b) Temperature and Speed of Hot Air

Hot air introduced to each drying chamber was set to have temperature of 180° C., dew point of 10° C., and wind speed of 1.6 [m/sec]. Meanwhile, direction of the hot air was from the bottom to the top of the dryer in the first chamber, while it was from the top to the bottom of the dryer in the second chamber to the sixth chamber.

(c) Through-Circulation Belt

As a through-circulation belt, a SUS 304 stainless belt that is a punching metal having staggered holes which are round and long shape with hole width of 1.2 mm and length of 15 mm and hole area ratio of 27% was used.

After the operation, the amount of the solid content of the hydrogel that is recovered from the inside of the dryer was 1.3% by weight relative to the amount of the solid content of the hydrogel that has been fed during the period.

The entire amount of the comparative dried product (2) was continuously supplied on a three-level roll mil (roll gap; from the top, 1.0 mm/0.55 mm/0.42 mm) for pulverizing. Thereafter, the size classification was carried out by using a screening device having wire mesh with a sieve mesh size of 850 μm. As a result, a comparative water absorbent resin (2) having the weight average particle diameter (D50) of 460 μm was obtained. Various physical properties such as CRC of the obtained comparative water absorbent resin (2) are summarized in the Table 1.

Example 4

As the aggregation treatment, hot air with temperature of 140° C. and dew point of 75° C., in which dew point is controlled by mixing steam, was blown, at the speed of 1.6 [m/sec], into the first chamber of a through-circulation belt type dryer. The direction of the hot air was from the bottom to the top of the dryer. Except for the operation above, the operations were carried out in the same manner as the Comparative example 2 to obtain a dried product (4).

After continuous operation for 1 month, it was found that the amount of the solid content of the hydrogel recovered from the inside of the dryer was 0.5% by weight relative to the amount of the solid content of the hydrogel that has been fed during the period.

The entire amount of the dried product (4) was pulverized and subjected to size classification in the same manner as the Comparative example 2. As a result, a water absorbent resin (4) having the weight average particle diameter (D50) of 450 μm was obtained. No adherents resulting from non-dried product were identified on the surface of the roll mill after pulverizing. Various physical properties of the obtained water absorbent resin (4) are summarized in the Table 1.

Comparative Example 3

Under the same conditions as the Comparative example 2, the through-circulation belt type dryer was continuously operated. After six months, 1 kg of the obtained comparative water absorbent resin (3) was extracted and monitored by visual examination. As a result, it was found that four grains of the water absorbent resin that are turned into yellow color or black color are included.

Example 5

Under the same conditions as the Comparative example 2, the through-circulation belt type dryer was continuously operated. Dropped residuals were removed from the dryer with frequency of one removal/month. After six months, 1 kg of the obtained water absorbent resin (5) was extracted and monitored by visual examination. However, no discolored water absorbent resin was found therein.

Example 6

Under the same conditions as the Comparative example 4, the through-circulation belt type dryer was continuously operated. Except that the frequency of removing dropped residuals was set to one removal/90 days, the same operation as the Example 5 was performed. After six months, 1 kg of the obtained water absorbent resin (6) was extracted and monitored by visual examination. However, no discolored water absorbent resin was found therein.

TABLE 1

|  | Comparative example 1 | Example 1 | Example 2 | Example 3 | Comparative example 2 | Example 4 |
|---|---|---|---|---|---|---|
| Particulate hydrogel crosslinked polymer | (1) | (1) | (1) | (1) | (2) | (2) |
| Monomer concentration [wt %] | 55 | 55 | 55 | 55 | 53 | 53 |
| Drop and scatter ratio [wt %] | 1.2 | 0.5 | 0.4 | 0.6 | 1.3 | 0.5 |
| Water absorbent resin | Comparative water absorbent resin (1) | Water absorbent resin (1) | Water absorbent resin (2) | Water absorbent resin (3) | Comparative water absorbent resin (2) | Water absorbent resin (4) |
| CRC [g/g] | 48 | 43 | 44 | 46 | 39 | 35 |
| Water extractables [wt %] | 24 | 14 | 14 | 18 | 15 | 10 |
| Residual monomers [ppm] | 200 | 150 | 150 | 190 | 400 | 200 |
| GEX value | 20.5 | 22.7 | 23.1 | 21.8 | 20.7 | 22.6 |

CONCLUSION

Both the Example 1 and the Comparative example 1 show the results obtained from a case in which a through-circulation stationary batch type dryer is used, and both the Example 4 and the Comparative example 2 show the results obtained from a case in which a through-circulation belt type dryer is used. However, according to the relation between the drop and scatter ratio and GEX value, the stationary batch type drying can be treated as a model of continuous type belt drying.

As shown in the Table 1, the drop and scatter ratio of hydrogel was 1.2% by weight and the obtained comparative water absorbent resin (1) contained 24% by weight of water extractables in the Comparative example 1, which is based on the Example 3 of U.S. Pat. No. 6,906,159 (monomer concentration: 55% by weight). On the other hand, in the Examples 1 to 3 aggregation treatment was carried out, it was possible to set the drop and scatter ratio of the hydrogel to 1% by weight or less. Further, an increase in water extractables during drying step after high concentration polymerization is suppressed, and as a result, a water absorbent resin having small amount of water extractables such as 14 to 18% by weight could be obtained. In the Comparative example 2 which corresponds to actual equipment, the drop and scatter ratio (2) of the hydrogel was 1.3% by weight and the obtained comparative water absorbent resin (2) contained 15% by weight of water extractables. On the other hand, in the Example 4 in which aggregation treatment was carried out, it was possible to set the drop and scatter ratio (2) of the hydrogel to 1% by weight or less, and also a water absorbent resin with small amount of water extractables could be obtained. As a result of examining initial phase color hue and color hue over time for the Examples 1 to 4, more favorable results were obtained compared to the Comparative examples.

The water absorbent resin obtained by the invention has little residual monomer, and by controlling the drop and scatter ratio to 1% by weight or less as illustrated in FIG. 1, the relative relation (GEX value) between CRC (water absorption capacity without load) and Ext (water extractables) is 21 or more, further 22 or more, particularly 23 or more, and therefore favorable.

INDUSTRIAL APPLICABILITY

According to the invention, a water absorbent resin having maintained/improved physical properties CRC (water absorption capacity without load) and Ext (water extractables) and others can be efficiently obtained even when a hydrogel with high solid content concentration is dried. Thus, according to the invention, productivity of a water absorbent resin can be improved, production cost can be lowered, and energy required for production step can be reduced (reduction of $CO_2$ emissions), or the like.

It should be noted that, the present application is based on Japanese Patent Application No. 2010-009812 filed on Jan. 20, 2010, Japanese Patent Application No. 2010-084024 filed on Mar. 31, 2010, and Japanese Patent Application No. 2010-055236 filed on Mar. 12, 2010, and the content of which is hereby incorporated by reference in its entirety into this application.

The invention claimed is:

1. A method for producing a water absorbent resin comprising:
   a polymerization step for polymerizing an unsaturated monomer; and
   a drying step for drying a particulate hydrogel crosslinked polymer having solid content concentration of 45% by weight or more, that is produced by micronization of the hydrogel cross linked polymer either during or after the polymerization, wherein
   a through-circulation belt dryer is used for drying in the drying step and drop and scatter ratio of the particulate hydrogel crosslinked polymer that is represented by following Formula 1 is set to 1% by weight or less:

Drop and scatter ratio[% by weight]={1−(Amount of solid content in particulate hydrogel obtained from drying step/Amount of solid content in particulate hydrogel provided to through-circulation belt)}×100, wherein an aggregation zone for aggregating the particulate hydrogel on the through-circulation belt is included for the drying step, and wherein the method for aggregating the particulate hydrogel during the aggregation zone comprises at least one of the following (1), (2), (3), and (5):

(1) ensuring aggregation time by suppressing drying speed at early phase of drying;

(2) promoting aggregation by increasing hygroscopic moisture within a drying chamber at early phase of drying;

(3) performing forced aggregation at early phase of drying by using a compression device; and (5) aggregating particulate hydrogel by cooling.

2. A method for producing a water absorbent resin comprising:

a polymerization step for polymerizing an unsaturated monomer; and a drying step for drying a particulate hydrogel crosslinked polymer having solid content concentration of 45% by weight or more, that is produced by micronization of the hydrogel crosslinked polymer either during or after the polymerization, wherein a through-circulation stationary batch dryer equipped with a through-circulation plate is used for drying in the drying step and drop and scatter ratio of the particulate hydrogel crosslinked polymer, that is represented by following Formula 2, is set to 1% by weight or less:

Drop and scatter ratio[% by weight]={1−(Amount of solid content in particulate hydrogel obtained from drying step/Amount of solid content in particulate hydrogel provided to through-circulation plate)}×100, wherein an aggregation zone for aggregating the particulate hydrogel on the through-circulation plate is included for the drying step, and wherein the method for aggregating the particulate hydrogel during the aggregation zone comprises at least one of the following (1), (2), (3), and (5):

(1) ensuring aggregation time by suppressing drying speed at early phase of drying;

(2) promoting aggregation by increasing hygroscopic moisture within a drying chamber at early phase of drying;

(3) performing forced aggregation at early phase of drying by using a compression device; and (5) aggregating particulate hydrogel by cooling.

3. The production method according to claim 1, wherein the method for aggregating the particulate hydrogel during the aggregation zone further comprises performing forced aggregation at early phase of drying by spraying an aggregating agent and the aggregated particulate hydrogel is dried at 150 to 250° C.

4. The production method according to claim 1, wherein the through-circulation belt type dryer has a multi-chamber structure and time period during which the increase amount of solid content concentration from the start of drying the particulate hydrogel is maintained within 10% by weight is 5 minutes or more.

5. The production method according to claim 1, wherein weight average particle diameter (D50) of the particulate hydrogel which is provided to the drying step is 1 mm or more.

6. The production method according to claim 1, wherein the solid content concentration of the particulate hydrogel is increased by vaporization of moisture during the polymerization step or addition of fine powder of a water absorbent resin.

7. The production method according to claim 1, wherein the hydrogel is provided on the through-circulation belt or the through-circulation plate such that average thickness of the particulate hydrogel is from 1 to 30 cm.

8. The production method according to claim 1, further comprising a step of recycling fine powder of a water absorbent resin or hydrated adduct thereof to the polymerization step or the drying step.

9. The production method according to claim 1, wherein the particulate hydrogel is contacted with a gas with dew point of 70 to 100° C. for 5 minutes or more and then dried by using a gas with dew point of 70° C. or less during the drying step.

10. The production method according to claim 1, wherein residuals generated by the particulate hydrogel that drops and/or scatters to an area other than the through-circulation belt or the through-circulation plate are periodically removed.

11. The production method according to claim 1, wherein the through-circulation belt or the through-circulation plate is a punching metal.

12. The production method according to claim 1, wherein the hole area ratio of the through-circulation belt or the through-circulation plate is from 20 to 50%.

13. The production method according to claim 1, wherein the polymerization during the polymerization step is either continuous kneader polymerization or continuous belt polymerization for vaporizing moisture.

14. A method for producing a water absorbent resin comprising:

a polymerization step for polymerizing an unsaturated monomer; and a drying step for drying a particulate hydrogel crosslinked polymer having solid content concentration of 45% by weight or more, that is produced by micronization of the hydrogel crosslinked polymer either during or after the polymerization, wherein a through-circulation belt type dryer is used for drying in the drying step and dropped residuals are periodically removed from the through-circulation belt type dryer.

15. The production method according to claim 14, wherein the drop and scatter ratio of the particulate hydrogel crosslinked polymer, that is represented by the following Formula 1, is set to 1% by weight or less:

Drop and scatter ratio[% by weight]={1−(Amount of solid content in particulate hydrogel obtained from drying step/Amount of solid content in particulate hydrogel provided to through-circulation belt)}×100.

16. The production method according to claim 14, wherein the dropped residuals are removed within 180 days of continuous operation.

17. The production method according to claim 1, wherein the solid content concentration in the particulate hydrogel crosslinked polymer is from 50 to 75% by weight.

18. The production method according to claim 2, wherein the method for aggregating the particulate hydrogel during the aggregation zone further comprises performing forced aggregation at early phase of drying by spraying an aggregating agent and the aggregated particulate hydrogel is dried at 150 to 250° C.

* * * * *